US011473096B2

(12) United States Patent
Pauli et al.

(10) Patent No.: US 11,473,096 B2
(45) Date of Patent: Oct. 18, 2022

(54) METHOD FOR DIFFERENTIATING CANNABIS PLANT CULTIVARS BASED ON CANNABINOID SYNTHASE PARALOGS

(71) Applicants: The Regents of the University of Colorado, A Body Corporate, Denver, CO (US); Steep Hill, Inc., Berkeley, CA (US)

(72) Inventors: Christopher Pauli, Boulder, CO (US); Kayia Clancy, Arvada, CO (US); Daniela Vergara, Louisville, CO (US); Nolan Coburn Kane, Boulder, CO (US); Reginald Gaudino, San Marcos, CA (US); Robert Givens, Buffalo, NY (US); Anthony C. Torres, Oakland, CA (US); Christian Cizek, Park City, UT (US)

(73) Assignees: The Regents of the University of Colorado, A Body Corporate, Denver, CO (US); Steve DeAngelo & Associates, LLC, Meadowbrook, PA (US)

( * ) Notice: Subject to any disclaimer, the term of this patent is extended or adjusted under 35 U.S.C. 154(b) by 55 days.

(21) Appl. No.: 16/753,325

(22) PCT Filed: Oct. 3, 2018

(86) PCT No.: PCT/US2018/054199
§ 371 (c)(1),
(2) Date: Apr. 2, 2020

(87) PCT Pub. No.: WO2019/070876
PCT Pub. Date: Apr. 11, 2019

(65) Prior Publication Data
US 2020/0270623 A1    Aug. 27, 2020

Related U.S. Application Data

(60) Provisional application No. 62/567,753, filed on Oct. 3, 2017.

(51) Int. Cl.
*C12N 15/82* (2006.01)
*C12P 7/22* (2006.01)
*C12P 17/06* (2006.01)
*C12Q 1/6895* (2018.01)

(52) U.S. Cl.
CPC .......... *C12N 15/8243* (2013.01); *C12P 7/22* (2013.01); *C12P 17/06* (2013.01); *C12Q 1/6895* (2013.01); *C12Q 2600/13* (2013.01)

(58) Field of Classification Search
CPC .............. C12Q 1/6895; C12Q 2600/13; C12Q 2600/156; C12Q 2600/158; C12Q 2600/16; C12Q 1/68; C12Q 1/6827; A01H 6/28
See application file for complete search history.

(56) References Cited

U.S. PATENT DOCUMENTS

| 4,683,195 A | 7/1987 | Mullis et al. |
| 4,683,202 A | 7/1987 | Mullis |
| 4,965,188 A | 10/1990 | Mullis et al. |
| 8,884,100 B2 | 11/2014 | Page et al. |
| 9,359,625 B2 | 6/2016 | Winnicki et al. |
| 9,765,308 B2 | 9/2017 | Page et al. |
| 2014/0057251 A1 | 2/2014 | McKernan |
| 2016/0177404 A1* | 6/2016 | McKernan ............... C12N 9/88 435/6.12 |
| 2017/0211049 A1 | 7/2017 | Page et al. |

FOREIGN PATENT DOCUMENTS

| JP | 2007020466 A | 2/2007 |
| WO | 2015/196275 A1 | 12/2015 |
| WO | 2015196275 A1 | 12/2015 |
| WO | 2016/189384 A1 | 12/2016 |
| WO | 2016189384 A1 | 12/2016 |
| WO | 2017/139496 A1 | 8/2017 |

OTHER PUBLICATIONS

Sirikantaramas et al. The gene controlling marijuana psychoactivity: molecular cloning and heterologous expression of Delta1-tetrahydrocannabinolic acid synthase from *Cannabis sativa* L. Journal of Biologiocal Chemistry. 2004. 38(17):39767-39774.*
de Meijer et al. The inheritance of chemical phenotype in *Cannabis sativa* L. (II): Cannabigerol predominant plants. Euphytica. 2005. 145: 189-198.*
Weiblen, George D., et al. "Gene duplication and divergence affecting drug content in Cannabis sativa." New Phytologist 208.4 (2015): 1241-1250. (Year: 2015).*
European Search Report issued in European Application No. 18864445.4 dated Jun. 8, 2021, 14 pages.
Kojoma et al., "DNA polymorphisms in the tetrahydrocannabinolic acid (THCA) synthase gene in "drug-type" and "fiber-type" *Cannabis sativa* L.," Forensic Science International, 2006, vol. 159, No. 2-3, pp. 132-140.
Kitamura et al., "Rapid identification of drug-type strains in Cannabis sativa using loop-mediated isothermal amplification assay," Journal of Natural Medicines, 2017, vol. 71, No. 1, pp. 86-95.
Bell et al., "The age and diversification of the angiosperms re-revisited," American Journal of Botany, vol. 97, No. 8, 2010, pp. 1296-1303.

(Continued)

*Primary Examiner* — Weihua Fan
(74) *Attorney, Agent, or Firm* — Mauriel Kapouytian Woods LLP; Elaine K. Lee

(57) ABSTRACT

Compositions and methods for providing desired cannabinoid content in cannabis plants. More particularly, the invention relates to compositions and methods for using cannabinoid synthase paralogs as guidance for breeding cannabis plants with a desired cannabinoid content, including but not limited to cultivars, varieties, lines and methods of breeding the same for commercial use.

19 Claims, 9 Drawing Sheets

Specification includes a Sequence Listing.

(56) References Cited

OTHER PUBLICATIONS

Bradbury et al., "TASSEL: software for association mapping of complex traits in diverse samples," Bioinformatics, vol. 23, No. 19, 2007, pp. 2633-2635.
Cheng et al., "Association mapping of agronomic and quality traits in USDA pea single-plant collection," Molecular Breeding, vol. 35, No. 2, 2015, 13 pages.
Chin et al., "Nonhybrid, finished microbial genome assemblies from long-read SMRT sequencing data," Nature Methods, vol. 10, No. 6, 2013, 10 pages.
De Meijer et al., "The inheritance of chemical phenotype in Cannabis sativa L.(II): cannabigerol predominant plants," Euphytica, vol. 145, No. 1-2, 2005, pp. 189-198.
De Meijer et al., "The inheritance of chemical phenotype in Cannabis sativa L.," Genetics, vol. 163, No. 1, 2003, pp. 335-346.
Delledonne et al., "Nitric oxide functions as a signal in plant disease resistance," Nature, vol. 394, No. 6693, 1998, pp. 585-588.
Elsohly et al., "Chemical constituents of marijuana: the complex mixture of natural cannabinoids," Life Sciences, vol. 78, No. 5, 2005, pp. 539-548.
Gagne et al., "Identification of olivetolic acid cyclase from Cannabis sativa reveals a unique catalytic route to plant polyketides," Proceedings of the National Academy of Sciences, vol. 109, No. 31, 2012, pp. 12811-12816.
Gaines et al., "Gene amplification confers glyphosate resistance in Amaranthus palmeri," Proceedings of the National Academy of Sciences, vol. 107, No. 3, 2010, 6 pages.
International Preliminary Report on Patentability issued in International Application No. PCT/US2018/054199 dated Apr. 16, 2020, 9 pages.
International Search Report and Written Opinion issued in International Application No. PCT/US2018/054199 dated Dec. 26, 2018, 12 pages.
Kumar et al., "MEGA7: molecular evolutionary genetics analysis version 7.0 for bigger datasets," Molecular Biology and Evolution, vol. 33, No. 7, 2016, pp. 1870-1874.
Langenheim, "Higher plant terpenoids: a phytocentric overview of their ecological roles," Journal of Chemical Ecology, vol. 20, No. 6, 1994, pp. 1223-1280.
Lynch et al., "Genomic and chemical diversity in Cannabis," Critical Reviews in Plant Sciences, vol. 35, No. 5-6, 2016, pp. 349-363.
McPartland et al., "Hemp diseases and pests: management and biological control: an advanced treatise," CABI, 2000, 276 pages.
Mills et al., "Studies on variant glucose-6-phosphate dehydrogenases: G6PD Fort Worth," Biochemical Medicine, vol. 13, No. 3, 1975, pp. 264-275.
Onofri et al., "Sequence heterogeneity of cannabidiolic- and tetrahydrocannabinolic acid-synthase in Cannabis sativa L. and its relationship with chemical phenotype," Phytochemistry, vol. 116, 2015, 12 pages.
Radwan et al., "Isolation and pharmacological evaluation of minor cannabinoids from high-potency Cannabis sativa," Journal of Natural Products, vol. 78, No. 6, 2015, pp. A-F.
Ravikumar et al., "Basal ganglionic angioleiomyoma," Clinical Neurology and Neurosurgery, vol. 98, No. 3, 1996, pp. 253-257.
Roy et al., "I-TASSER: a unified platform for automated protein structure and function prediction," Nature Protocols, vol. 5, No. 4, 2010, pp. 725-738.
Russo, "Taming THC: potential cannabis synergy and phytocannabinoid-terpenoid entourage effects," British Journal of Pharmacology, vol. 163, No. 7, 2011, pp. 1344-1364.
Russo et al., "Cannabis is more than simply Δ 9-tetrahydrocannabinol," Psychopharmacology, vol. 165, No. 4, 2003, pp. 431-432.
Shoyama et al. "Structure and function ofΔ 1-tetrahydrocannabinolic acid (THCA) synthase, the enzyme controlling the psychoactivity of Cannabis sativa," Journal of Molecular Biology, vol. 423, No. 1, 2012, pp. 96-105.
Shoyama et al., "Biosynthesis of cannabinoid acids," Phytochemistry, vol. 14, No. 10, 1975, pp. 2189-2192.
Singh et al., "Transcription factors in plant defense and stress responses," Current Opinion in Plant Biology, vol. 5, No. 5, 2002, pp. 430-436.
Sirikantaramas et al., "Tetrahydrocannabinolic acid synthase, the enzyme controlling marijuana psychoactivity, is secreted into the storage cavity of the glandular trichomes," Plant and Cell Physiology, vol. 46, No. 9, 2005, pp. 1578-1582.
Soltis et al., "Book Review-//Phylogeny and Evolution of Angiosperms," International Journal of Plant Sciences, vol. 167, No. 3, May 2006, pp. 607-611.
Staginnus et al., "A PCR marker Linked to a THCA synthase Polymorphism is a Reliable Tool to Discriminate Potentially THC-Rich Plants of C annabis sativa L.," Journal of Forensic Sciences, vol. 59, No. 4, 2014, pp. 919-926.
Swift et al., "Analysis of cannabis seizures in NSW, Australia: cannabis potency and cannabinoid profile," PloS One, vol. 8, Issue 7, Jul. 2013, e70052, pp. 1-9.
Taura et al., "Characterization of olivetol synthase, a polyketide synthase putatively involved in cannabinoid biosynthetic pathway," FEBS Letters, vol. 583, No. 12, 2009, pp. 2061-2066.
Untergasser et al., "Primer3—new capabilities and interfaces," Nucleic Acids Research, vol. 40, No. 15, 2012, e115, 12 pages.
Van Bakel et al., "The draft genome and transcriptome of Cannabis sativa," Genome Biology, vol. 12, No. 10, 2011, R102, pp. 1-17.
Vergara et al.,"Genetic and Genomic Tools for Cannabis sativa," Critical Reviews in Plant Sciences, vol. 35, No. 5-6, pp. 1-14.
Weiblen et al., "Gene duplication and divergence affecting drug content in Cannabis sativa," New Phytologist, vol. 208, No. 4, 2015, pp. 1241-1250.
Wheeler et al., "Database resources of the national center for biotechnology information," Nucleic Acids Research, vol. 31, No. 1, 2003, pp. 28-33.
Yang et al., "The I-TASSER Suite: protein structure and function prediction," Nature Methods, vol. 12, No. 1, 2015, 5 pages.
Yu et al., "Genetic association mapping and genome organization of maize," Current Opinion in Biotechnology, vol. 17, No. 2, 2006, pp. 155-160.
Zhu et al., "Status and prospects of association mapping in plants," The Plant Genome, vol. 1, No. 1, 2008, pp. 5-20.
Zmienko et al., "Copy number polymorphism in plant genomes," Theoretical and Applied Genetics, vol. 127, No. 1, 2014, pp. 1-18.

* cited by examiner

| AA in Synthase | 99 | 116 | 118 | 139 | 146 | 147 | 148 | 149 | 160 | 165 | 172 | 173 | 180 | 182 | 186 | 192 | 193 |
|---|---|---|---|---|---|---|---|---|---|---|---|---|---|---|---|---|---|
| ACDC | C | S | G | K | F | A | W | Y | K | A | A | C | A | G | P | R |
| Otto | C | S | G | N | I | A | R | Y | D | K | A | A | G | A | G | P | Q |
| Durban Poison | C | S | G | K | F | A | W | Y | K | G | A | C | A | G | P | * |
| DX0395F | W | S | G | N | I | A | R | Y | K | A | A | C | A | G | P | Q |
| Harlequin | C | S | G | K | F | A | W | Y | K | A | A | C | A | G | P | R |
| Blue Dream | C | S | G | N | I | A | R | Y | K | A | A | C | A | G | P | Q |
| Chemdawg | C | S | G | K | F | A | W | Y | D | K | A | A | C | A | G | P | * |
| OG 18 | C | S | G | N | I | A | R | Y | K | A | A | C | A | G | P | Q |
| Super Lemon Haze | C | A | G | K | F | A | W | Y | K | G | A | G | G | P | A | R |
| Pre-98 Bubba Kush | C | K | G | K | T | A | W | Y | M | A | G | G | G | S | A | R |
| AB292682 | C | S | G | K | F | A | W | Y | A | K | A | A | C | G | G | P | K |

*FIG. 3A*

| AA in Synthase | 451 | 454 | 457 | 465 | 474 | 479 | 485 | 496 |
|---|---|---|---|---|---|---|---|---|
| ACDC | Q | M | H | Y | D | T | D | D |
| AK47 | H | K | Y | D | D | T | H | D |
| Blue Dream | H | N | Y | D | D | T | H | D |
| Chem Dawg x Mass x NL5 | H | K | Y | D | D | T | H | D |
| Chem Dawg | H | K | Y | D | D | T | H | D |
| Durban Poison | H | K | Y | D | D | T | H | D |
| Girl Scout Cookies | H | K | Y | D | D | T | H | D |
| Golden Goat | H | K | Y | D | D | T | H | D |
| Gumbi | H | K | Y | D | D | T | H | D |
| Harlequin | H | K | Y | D | D | T | H | D |
| Kunduz | H | K | Y | D | D | T | H | D |
| LA OG | H | K | Y | D | D | T | H | D |
| OG 18 | H | K | Y | D | D | T | H | D |
| Petrolia | H | K | Y | D | D | T | H | D |
| Pre-98 Bubba Kush | H | K | Y | D | D | T | H | D |
| Super Lemon Haze | H | K | Y | D | D | T | H | D |
| White Widow | H | K | Y | D | D | T | H | D |
| AB292821 | Q | N | H | Y | K | A | D | E |

FIG. 3B

| AA in Synthase | 116 | 165 | 172 | 173 | 180 | 186 | 192 | 218 | 225 | 243 |
|---|---|---|---|---|---|---|---|---|---|---|
| 707 Headband | A | M | P | G | G | S | A | D | D | ? |
| AC/DC | A | K | P | G | G | S | A | D | D | A |
| BlackDiesel | A | K | P | G | G | S | A | D | D | A |
| Blue Dream | A | M | P | G | G | S | A | D | D | ? |
| C1 | A | K | P | G | G | S | A | D | D | A |
| C2 | A | M | P | G | G | S | A | D | D | A |
| C3 | A | K | P | G | G | S | A | D | D | A |
| C6 | A | K | P | G | G | S | A | D | D | A |
| C14 | A | K | P | G | G | S | A | D | D | A |
| C16 | A | K | P | G | G | S | A | D | D | A |
| K2 | A | K | P | G | G | S | A | D | D | A |
| K3 | A | K | P | G | G | S | A | D | D | A |
| K9 | A | K | P | G | G | S | A | D | D | A |
| K19 | A | ? | P | A | G | G | P | Q | N | D |
| Cherri Dawg | A | K | P | G | G | S | A | D | D | A |
| Durban Poison | A | M | P | G | G | S | P | D | D | A |
| Girl Scout Cookies | A | K | P | G | G | S | A | D | D | ? |
| Golden Goat | A | K | P | A | G | G | P | D | D | A |
| Gumbo | A | M | P | G | G | S | A | D | D | A |
| Harlequin | A | M | P | G | G | S | ? | D | ? | A |
| E330JD | A | K | P | G | G | S | A | D | D | A |
| KumKuz | A | K | P | G | G | S | P | D | N | A |
| LA OG | A | K | P | G | G | S | A | D | D | A |
| OG 18 | A | M | P | G | G | S | ? | D | D | A |
| Otto | A | K | P | G | G | S | P | D | N | A |
| Pre-98 Bubba Kush | A | K | P | G | G | S | A | D | D | A |
| Super Lemon Haze | A | K | P | A | G | G | P | N | N | P |

*FIG. 3C*

METHOD FOR DIFFERENTIATING CANNABIS PLANT CULTIVARS BASED ON CANNABINOID SYNTHASE PARALOGS

CROSS REFERENCE TO RELATED APPLICATIONS

This application is a 371 of International Application No. PCT/US2018/054199, filed Oct. 3, 2018, which claims the benefit of U.S. Provisional Patent Application Ser. No. 62/567,753, filed Oct. 3, 2017. The entire contents of these applications are hereby incorporated herein by reference.

INCORPORATION OF SEQUENCE LISTING

A computer readable form of the Sequence Listing, 10102-2000100SequenceListing.txt (43,000 bytes), submitted via EFS-WEB and amended on Apr. 2, 2020, is herein incorporated by reference in its entirety.

TECHNICAL FIELD

This invention relates generally to the fields of genetic technology and botany. In particular, the present invention relates to cannabinoid synthase genes, paralogs thereof, and uses thereof.

BACKGROUND

Cannabis is an angiosperm from the family cannabacea that has been cultivated for thousands of years for multiple purposes, including, in particular, the production of secondary metabolites known as cannabinoids. Cannabis cultivation is now a multibillion dollar industry that centers on the two most well-known cannabinoids; delta-9-tetrahydrocannabinolic acid (THCA) and Cannabidolic acid (CBDA). THCA is most commonly associated with psychoactive effects. CBDA has gained popularity for its non-psychoactive medicinal uses. THCA and CBDA are the final products of a three-step biochemical pathway. The last step in the pathway is catalyzed by the enzymes THCA and CBDA synthase, respectively.

Duplication and deletion of genomic regions may result in gene copy number (CN) variation or paralogs, which have been shown to be common in plant genes related to stress or disease resistance (Delledonne et al. 1998; Gaines et al. 2010; Żmieńko et al. 2014). It has been proposed that the ecological function of cannabinoids is to protect the plant from external stressors (ie. UV light, herbivory, & pathogens) (Langenheim 1994; McPartland et al. 2000; Sirikantaramas et al. 2005), and the genes coding for these cannabinoid synthases are found in multiple, divergent paralogs (Onofri et al. 2015) that vary in CN and alleles between and within lineages. An example of a particularly significant variation is the preeminence of functionally-compromised CBDAS alleles among high-THCA cultivars (Onofri et al. 2015). Complex traits such as cannabinoid content often consist of multiple loci that make it difficult to determine their location or copy number. Due to sequence similarity, determining their sequence is problematic.

Therefore, there is a need for accurate methods of identifying distinct cannabinoid synthase paralogs and determining paralog copy number in a cannabis cultivar to guide the cultivation of cannabis cultivars having specific cannabinoid contents and concentrations.

SUMMARY

The inventors have developed specific PCR primers and probes that amplify unique regions within cannabinoid synthase paralogs (CBDA synthases) that are directly responsible for the production of CBDA in the cannabis plant. The inventors have also found SNPs in the amplified regions of these cannabinoid synthase paralogs and other possible SNPs throughout the whole cannabis plant genome that influence cannabinoid production.

Thus, this disclosure provides a method for producing a cannabis plant cultivar, including identifying paralogs of a cannabinoid synthase gene in two or more cannabis plant cultivars; and crossbreeding two individual cannabis plant cultivars identified to have desired effects on cannabinoid production in the cannabis plant. In these methods, the cannabinoid synthase gene may be selected from delta-9-tetrahydrocannabinolic acid (THCA) and Cannabidolic acid (CBDA) synthase. In these methods, the cannabinoid synthase gene may be the CBDA synthase gene.

In these methods, the identifying step may comprise PCR amplification of a composition comprising genomic DNA from the two or more cannabis plant cultivars. In these methods, the identifying step may comprise PCR amplification using a primer set selected from the group consisting of:

```
F:
                                      (SEQ ID NO: 13)
    5' TCACCTCTAACACAACCCCAAAA 3'

R:
                                      (SEQ ID NO: 14)
    5' CCAAAAGAGATCTTCCCCCATA 3',
and F:
                                      (SEQ ID NO: 15)
    5' GCGTTGTACCCTTACGGTTG 3'

R:
                                      (SEQ ID NO: 16)
    5' TTTTGACTCTTGGGATCATTTATTC 3'.
```

In these methods, the crossbreeding may select for a cannabis plant cultivar having a greater CBDA content than the two identified individual cannabis plant cultivars. Alternatively or additionally, the crossbreeding may select for a cannabis plant cultivar having a lower CBDA content than the two identified individual cannabis plant cultivars. In these methods, the CBDA content of the *cannabis* plant cultivar resulting from the crossbreeding step may result from i) greater enzymatic activity of a CBDA paralog identified in two or more cannabis plant cultivars, and/or ii) greater copy number of a CBDA. In these methods, the cannabinoid content of the cannabis plant cultivar resulting from the crossbreeding step is a result of a protein selected from a protein listed in Table 3 of this disclosure. In these methods, the identified paralog may be at least one of paralogs 008242 and/or 00395.

In these methods, the crossbreeding may also include crossing a first *cannabis* plant wherein the first cannabis plant provides desired cannabinoid content, with a second cannabis plant, and harvesting the resultant hybrid cannabis seed. Alternatively or additionally, the crossbreeding may include introgressing CBDA production into hybrid cannabis seeds. The crossbreeding may also include one or more of a backcrossing, an outcrossing, and a self-crossing.

In these methods, the cannabis cultivar may comprise one or more DNA molecular markers associated with CBDA synthase activity. Thus, in these methods, the identification of paralogs of a cannabinoid synthase gene may also include molecular marker analysis of DNA samples isolated from one or more of a progeny plant, a second cannabis plant, a high CBDA producing cannabis cultivar, a parental cannabis cultivar, and a low CBDA producing cannabis cultivar, wherein said analysis identifies DNA molecules associated with CBDA content in the cannabis plant. In these methods, the molecular marker may include a single nucleotide polymorphism (SNP). In these methods, the molecular marker may encode at least one amino acid substitution identified in the CBDA synthase gene selected from the amino acid substitutions set forth in FIGS. 3A-3C of this disclosure.

This disclosure also provides a cannabis plant cultivar produced by the methods of this disclosure. These cannabis plant cultivars may be obtained by crossbreeding two individuals selected from the group consisting of the cultivar produced by the methods of this disclosure, and a progeny of such cultivar.

This disclosure also provides a PCR primer selected from the group consisting of

```
                                           (SEQ ID NO: 13)
    5' TCACCTCTAACACAACCCCAAAA 3'

(SEQ ID NO: 14)
    5' CCAAAAGAGATCTTCCCCCATA 3'

(SEQ ID NO: 15)
    5' GCGTTGTACCCTTACGGTTG 3',
    and (SEQ ID NO: 16)
    5' TTTTGACTCTTGGGATCATTTATTC 3'.
```

This disclosure also provides a composition comprising the PCR primer set

```
                                           (SEQ ID NO: 13)
    5' TCACCTCTAACACAACCCCAAAA 3'
    and (SEQ ID NO: 14)
    5' CCAAAAGAGATCTTCCCCCATA 3'.
```

This disclosure also provides a composition comprising the PCR primer set

```
                                           (SEQ ID NO: 15)
    5' GCGTTGTACCCTTACGGTTG 3'
    and (SEQ ID NO: 16)
    5' TTTTGACTCTTGGGATCATTTATTC 3'.
```

Kits and conditions useful in conducting the assays are also provided.

This Summary is neither intended nor should it be construed as being representative of the full extent and scope of the present invention. Moreover, references made herein to "the present disclosure," or aspects thereof, should be understood to mean certain embodiments of the present disclosure and should not necessarily be construed as limiting all embodiments to a particular description. The present invention is set forth in various levels of detail in this Summary as well as in the attached figures and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the figures.

BRIEF DESCRIPTION OF FIGURES

(FIG. 1A) c395, (FIG. 1B) c8242, and (FIG. 1C) d589 and a full length berberine-bridge containing enzymes with a 100-bootstrap support. Branches with less than 70% bootstrap support are collapsed. Eighteen sequences of 342 nt, 23 sequences of 236 nt, and 31 sequences of 448 nt were input to MEGA for the c395, c8242, and d589 primer sets respectively. All trees included the studied paralogs (0395.1, 0745.1, 8229.1, and 1769.1 from the PBBK assembly) and outgroups (E33090.1, AB292682.1, and 2 CBCAS genes) for comparison between the trees.

FIGS. 1A and 1B show the variation in five positions for the amplicons from primer c395. FIGS. 1C and 1D show the variation in nine positions in the amplified region by primer c8242. FIGS. 1E and 1F show the variation in four positions for the amplified region produced by primer d589. For each site shown at the bottom of the panels, the common nucleotide is shown in parenthesis, which when replaced with the mutant base produces a positive or negative effect on cannabinoid content. The notation used in the legend for SNP designation is "location in gene-mutant base (wild-type base)". Bars that have more than one position represent nucleotides with the same normalized effect size.

FIGS. 3A-3C show tables of Amino Acid Substitutions in Amplified Regions: Only the non-synonymous amino acid substitutions that were observed from the inventors' amplicons are shown in single letter amino acid code for the c395 (FIG. 3A), c8242 (FIG. 3B), and d589 (FIG. 3C) amplified regions. Amino add sites that were conserved between cultivars are not shown in the tables, nor are the SNPs encoding these non-synonymous substitutions. The positions are listed in reference to the published gene for THCAS/CBDAS listed by accession number on the tables (E33090/AB292682.1). The light and dark gray highlighting of amino acid sites show the minor allelic variants of these synthase genes. A question mark (?) denotes an amino acid that could not be determined due to an ambiguous sanger sequencing or a heterozygote site. An asterisk (*) signifies that an internal stop codon was present within the amplified region. All cultivars amplified by the primers were used in this analysis; however, some varieties were eliminated from the downstream analysis due to the lack of chemotypic or relationship data.

DETAILED DESCRIPTION

Figure 1A:
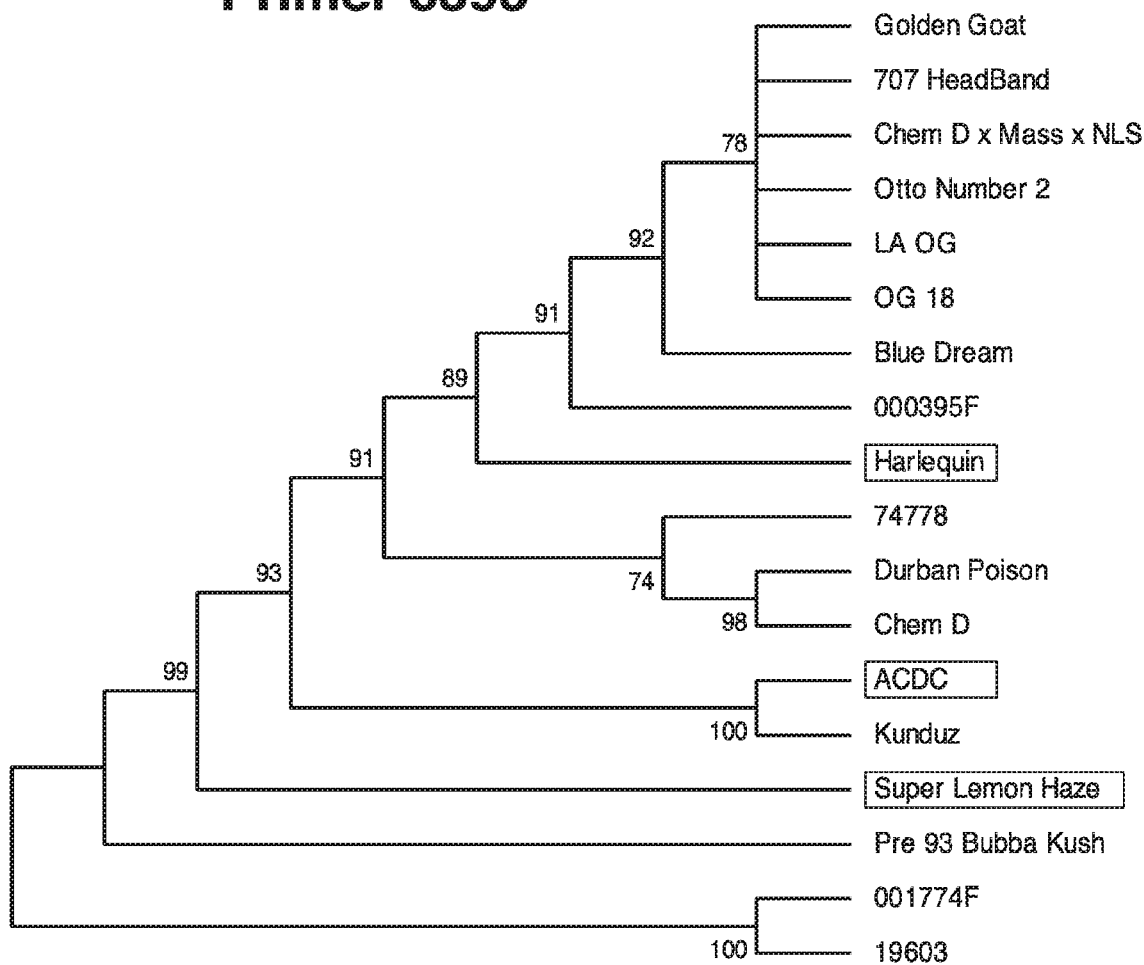
FIGS. 1A-1C show the Neighbor-Joining Trees constructed for each primer set.

To facilitate an understanding of the present invention, a number of terms and phrases are defined below:

The use of the article "a" or "an" is intended to include one or more.

As used herein, the term "cannabis" refers to any flowering plant in the family Cannabaceae. This may include the species *Cannabis sativa*, *Cannabis indica*, and *Cannabis ruderalis*.

As used herein, the term "plant" is used in it broadest sense. It includes, but is not limited to, any species of woody, ornamental or decorative, crop or cereal, fruit or vegetable, fruit plant or vegetable plant, flower or tree, macroalga or microalga, phytoplankton and photosynthetic algae (e.g., green algae Chlamydomonas reinhardtii). A plant also refers to a unicellular plant (e.g. microalga) and a plurality of plant cells that are largely differentiated into a colony (e.g. volvox) or a structure that is present at any stage of a plants development Such structures include, but are not limited to, a fruit, a seed, a shoot, a stem, a leaf, etc.

As used herein, the term "seed" refers to a fertilized and ripened ovule of a plant, consisting of an embryo and a casing.

As used herein, the term "hybrid" in reference to a seed or plant is produced as the result of controlled cross-pollination as opposed to a non-hybrid seed produced as the result of natural pollination, as in a "hybrid cannabis seed" produced by breeding methods of the present invention.

The terms "leaf" and "leaves" refer to a usually flat, green structure attached to a stem or branch of a plant wherein photosynthesis and transpiration take place.

The term "stem" refers to a main ascending axis of a plant.

"Node" refers to the joint of a stem and the region of attachment of leaves on a stem.

As used herein, the term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" refers to a plant structure or a plant tissue, for example, pollen, an ovule, a tissue, a pod, a seed, and a cell. In some embodiments of the present invention transgenic plants are crop plants.

As used herein, the term "line" refers to a nursery term to describe a group of individuals from similar parentage with similar traits.

As used herein, the term "cultivar" refers to an unvarying variety of plant propagated by man using selective hybridization and maintained by vegetative propagation or by inbred seed.

As used herein, the term "cannabis cultivar" is used in its broadest sense and includes but is not limited to any species of cannabis that is cultivated by man.

As used herein, the term "cultivated" in reference to a plant includes any plant or plant part grown and maintained by man for use in food compositions or in nonfood compositions.

As used herein, the terms "variety" and "varietas" refer to a rank of taxa below subspecies but above forma for example a plant which retains most of the characteristics of the species, but differs in some way, such as CBDA content or THCA content.

As used herein, the terms "F-generation" and "filial generation" refers to any of the consecutive generations of cells, tissues or organisms after a biparental cross. The generation resulting from a mating of the a biparental cross (i.e. parents) is the first filial generation (designated as "F1") in reference to a seed and it's plant, while that resulting from crossing of F1 individuals is the second filial generation (designated as "F2") in reference to a seed and it's plant. For example, an F2 seed and a resulting plant are produced by self-pollination of F1, while later F generations are produced from self-pollination of the immediate prior generation.

As used herein, the terms "germplasm" refers to any genetic material of plants, animals or other organisms containing functional units of heredity.

As used herein, the term "hybrid" refers to a seed and a plant produced as the result of controlled pollination as opposed to a seed and a plant produced as the result of natural pollination.

As used herein, the term "trait" refers to an observable and/or measurable characteristic of an organism, such as a trait of a plant, for example, THCA production or CBDA production.

As used herein, the terms "marker" and "DNA marker" and "molecular marker" in reference to a "selectable marker" refers to a physiological or morphological trait which may be determined as marker for its own selection or for selection of other traits closely linked to that marker, for example, a gene or trait that associates with aphid resistance, such as a marker, such as a DNA marker including but not limited to simple sequence repeat (SSR), single nucleotide polymorphism analysis (SNP), random amplified polymorphic DNA analysis (RAPID), amplified fragment length polymorphism analysis (AFLP), and the like that will link phenotype information, such as aphid resistance to a QTL locus, to provide a genomic map, for example a fingerprint map, and chromosome location and/or map.

As used herein, the term "linkage group" refers to a group of two or more genetically or physically mapped loci with observed linkage to a trait, for example, one or more of a SSR, SNP, AFLP, and RAPD marker of the present invention that may map to CBDA production.

As used herein, the term "selection" refers to the process of determining the relative cannabinoid production of a cannabis cultivar.

As used herein, the term "introgress" and "introgressing" refers to incorporating a genetic substance, such as germplasm, loci, allele, gene, DNA, and the like for introducing a trait into an organism, such as a plant, a cannabis cultivar and the like, for example, incorporating aphid resistant germplasm into a previously aphid susceptible plant variety. Introgression may refer to a breeding method for incorporating a genetic trait, such as aphid resistance, including compositions and methods for using QTL, DNA markers including but not limited to simple sequence repeat (SSR), single nucleotide polymorphism analysis (SNP), random amplified polymorphic DNA (RAPD), amplified fragment length polymorphism analysis (AFLP), DNA fingerprinting, and the like for incorporating CBDA and/or THCA production germplasm into a plant variety.

As used herein, the terms "quantitative trait locus" and "QTL" refer to a genomic region including a gene underlying a trait on which many genes act.

As used herein, the terms "simple sequence repeat" and "SSR" refer to short, tandem repeat nucleotide sequences that are useful as genetic markers, for example, microsatellite DNA is a highly polymorphic DNA marker comprised of mononucleotides, dinucleotides, trinucleotides or tetranucleotides that are repeated in tandem arrays and distributed throughout the genome, such as CA (alternatively GT) dinucleotide repeats.

As used herein, the terms "single nucleotide polymorphism" and "SNP" refer to a single base difference between two DNA sequences.

As used herein, the terms "random amplified polymorphic DNA" and "RAPD" refer to a common technique for amplifying anonymous stretches of DNA using PCR with arbitrary primers, for example, using random PCR primers used to amplify genomic DNA to provide a pattern of bands, such that one pattern of bands may be different between individuals in a population, such as between aphid resistant and aphid susceptible plants or show germplasm differences between closely related plants.

As used herein, the terms "restriction fragment length polymorphism" and "RFLP" refer to genetic variation between individuals such that DNA fragment sizes resulting from a difference in DNA sequence that affects the recognition sequence for restriction enzymes when cut by specific restriction enzymes. When a particular enzyme digests DNA the fragment sizes will differ depending on the presence or absence of the proper recognition sequence for the enzyme. Polymorphic sequences that result in RFLPs are used as markers on both physical maps and genetic linkage maps. RFLPs can be caused by a change in at least one nucleotide at a cutting site.

As used herein, the terms "amplified fragment length polymorphism" and "AFLP" refer to a highly sensitive method for detecting polymorphisms in DNA. Following restriction enzyme digestion of DNA, a subset of DNA fragments is selected for PCR amplification and visualization.

As used herein, the term "DNA fingerprinting" refers to techniques for uniquely identifying an individual among a population based on one's DNA. This type of method of isolating and visualizing sequences of DNA may show a unique pattern of DNA fragments revealed by Southern hybridization or by a polymerase chain reaction (PCR) analysis.

As used herein, the term "polymerase chain reaction" and "PCR" refer to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "gene" refers to a nucleic acid (e.g., DNA or RNA) sequence that comprises coding sequences necessary for the production of RNA, or a polypeptide or its precursor (e.g., proinsulin). A functional polypeptide can be encoded by a full-length coding sequence or by any portion of the coding sequence as long as the desired activity or functional properties (e.g., enzymatic activity, ligand binding, signal transduction, etc.) of the polypeptide are retained. As used herein, the term "gene" encompasses the coding regions of a structural gene and includes sequences located adjacent to the coding region on both the 5' and 3' ends for a distance of about 1 kb on either end such that the gene corresponds to the length of the full-length mRNA.

As used herein, the term "portion" when used in reference to a gene refers to fragments of that gene. The fragments may range in size from a few nucleotides to the entire gene sequence minus one nucleotide.

As used herein, the term "a nucleotide comprising at least a portion of a gene" may comprise fragments of the gene or the entire gene.

As used herein, the terms "allele" and "alleles" refer to each version of a gene for a same locus that has more than one sequence. For example, there are multiple alleles for eye color at the same locus.

As used herein, the terms "recessive," "recessive gene," and "recessive phenotype" refers to an allele that has a phenotype when two alleles for a certain locus are the same as in "homozygous" or as in "homozygote," and then partially or fully loses that phenotype when paired with a more dominant allele when two alleles for a certain locus are different as in "heterozygous" or in "heterozygote."

As used herein, the terms "dominant," and "dominant phenotype" refers to an allele that has an effect to suppress the expression of the other allele in a heterozygous (having one dominant and one recessive allele) condition.

As used herein, the term "heterologous" when used in reference to a gene or nucleic acid refers to a gene that has been manipulated in some way. For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Examples of a heterologous gene includes a gene encoding an insecticidal protein, an herbicide resistant protein, or for providing an agronomic trait. Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

As used herein, the term "nucleic acid sequence," "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

As used herein, the term "cDNA" refers to a nucleotide copy of the "messenger RNA" or "mRNA" for a gene. In some embodiments, cDNA is derived from the mRNA. In some embodiments, cDNA is derived from genomic sequences.

As used herein, the term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "polynucleotide" refers to refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

As used herein, the term "an oligonucleotide having a nucleotide sequence encoding a gene" or "a nucleic acid sequence encoding" a specified polypeptide refers to a nucleic acid sequence comprising the coding region of a gene or in other words the nucleic acid sequence that encodes a gene product. The coding region may be present either in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc. or a combination of both endogenous and exogenous control elements.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment), *Agrobacterium* infection, and the like.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

As used herein, the terms "modified" or "mutant" when made in reference to a gene or to a gene product refers, respectively, to a gene or to a gene product which displays modifications in sequence and/or functional properties (i.e., altered characteristics) when compared to the wild-type gene or gene product. Thus, the terms "variant" and "mutant" when used in reference to a nucleotide sequence refer to a nucleic acid sequence that differs by one or more nucleotides from another, usually related nucleotide sequence. A "variation" is a difference between two different nucleotide sequences; typically, one sequence is a reference sequence.

As used herein, the term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" and "SNP" refers a genetic locus of a single base that may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

As used herein, the terms "protein," "polypeptide," "peptide," "encoded product," "amino acid sequence," are used interchangeably to refer to compounds comprising amino acids joined via peptide bonds. A "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include, but are not limited to, glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence.

As used herein, the term "isolated" when used in relation to a nucleic acid such as an isolated DNA molecule or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain, at a minimum, the sense or coding strand (i.e., the oligonucleotide may single-stranded), but may contain both the sense and anti-sense strands (i.e., the oligonucleotide may be double-stranded).

As used herein, the term "purified" refers to molecules, either nucleic or amino acid sequences, that are removed from their natural environment, isolated, or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

As used herein, the term "portion" when used in reference to a protein (as in "a portion of a given protein") refers to fragments of that protein. The fragments may range in size from four amino acid residues to the entire amino sequence minus one amino acid.

As used herein, the term "positional cloning" refers to an identification of a gene based on its physical location in the genome.

This disclosure contains the following Sequences

| SEQ ID NO | Description | Sequence |
|---|---|---|
| 1 | Nucleotide Sequence of Paralog "001774F" THCA Synthase | ATGAATTGCTCAGCATTTTCCTTTTGGTTTGTTTGCAAAATAATATTTTT<br>CTTTCTCTCATTCCATATCCAAATTTCAATAGCTAATCCTCGAGAAAAC<br>TTCCTTAAATGCTTCTCAAAACATATTCCCAACAATGTAGCAAATCCAA<br>AACTCGTATACACTCAACACGACCAATTGTATATGTCTATCCTGAATTC<br>GACAATACAAAATCTTAGATTCATCTCTGATACAACCCCAAAACCACTC<br>GTTATTGTCACTCCTTCAAATAACTCCCATATCCAAGCAACTATTTTAT<br>GCTCTAAGAAAGTTGGCTTGCAGATTCGAACTCGAAGCGGTGGCCAT<br>GATGCTGAGGGTATGTCCTACATATCTCAAGTCCCATTTGTTGTAGTA<br>GACTTGAGAAACATGCATTCGATCAAAATAGATGITCATAGCCAAACT<br>GCGTGGGTTGAAGCCGGAGCTACCCTTGGAGAAGTTTATTATTGGATC<br>AATGAGAAGAATGAGAATCTTAGTTTTCCTGGTGGGTATTGCCCTACT<br>GTTGGCGTAGGTGGACACTTTAGTGGAGGAGGCTATGGAGCATTGAT<br>GCGAAATTATGGCCTTGCGGCTGATAATATTATTGATGCACACTTAGT<br>CAATGTTGATGGAAAAGTTCTAGATCGAAAATCCATGGGAGAAGATCT<br>GTTTTGGGCTATACGTGGTGGTGGAGGAGAAAACTTTGGAATCATTGC<br>AGCATGGAAAATCAAACTGGTTGCTGTCCCATCAAAGTCTACTATATTC<br>AGTGTTAAAAAGAACATGGAGATACATGGGCTTGTCAAGTTATTTAACA<br>AATGGCAAAATATTGCTTACAAGTATGACAAAGATTTAGTACTCATGAC<br>TCACTTCATAACAAAGAATATTACAGATAATCATGGGAAGAATAAGACT<br>ACAGTACATGGTTACTTCTCTTCAATTTTTCATGGTGGAGTGGATAGTC<br>TAGTCGACTTGATGAACAAGAGCTTTCCTGAGTTGGGTATTAAAAAAA<br>CTGATTGCAAAGAATTTAGCTGGATTGATACAACCATCTTCTACAGTGG<br>TGTTGTAAATTTTAACACTGCTAATTTTAAAAAGGAAATTTTGCTTGATA<br>GATCAGCTGGGAAGAAGACGGCT7TCTCAATTAAGTTAGACTATGTTA<br>AGAAACCAATTCCAGAAACTGCAATGGTCAAAATTTTGGAAAAATTATA<br>TGAAGAAGATGTAGGAGCTGGGATGTATGTGTTGTACCCTTACGGTG |

-continued

| SEQ ID NO | Description | Sequence |
|---|---|---|
| | | GTATAATGGAGGAGATTTCAGAATCAGCAATTCCATTCCCTCATCGAG<br>CTGGAATAATGTATGAACTTTGGTACACTGCTTCCTGGGAGAAGCAAG<br>AAGATAATGAAAAGCATATAAACTGGGTTCGAAGTGTTTATAATTTTAC<br>GACTCCTTATGTGTCCCAAAATCCAAGATTGGCGTATCTCAATTATAGG<br>GACCTTGATTTAGGAAAAACTAATCATGCGAGTCCTAATAATTACACAC<br>AAGCACGTATTTGGGGTGAAAAGTATTTTGGTAAAAATTTTAACAGGTT<br>AGTTAAGGTGAAAACTAAAGTTGATCCCAATAATTTTTTTAGAAACGAA<br>CAAAGTATCCCACCTCTTCCACCGCATCATCATTAA |
| 2 | Amino Acid Sequence of Paralog "001774F" THCA Synthase | MNCSAFSFWFVCKIIFFFLSFHIQISIANPRENFLKCFSKHIPNNVANPKLVY<br>TQHDQLYMSILNSTIQNLRFISDTTPKPLVIVTPSNNSHIQATILCSKKVGLQ<br>IRTRSGGHDAEGMSYISQVPFVVVDLRNMHSIKIDVHSQTAWVEAGATLG<br>EVYYWINEKNENLSFPGGYCPTVGVGGHFSGGGYGALMRNYGLAADNII<br>DAHLVNVDGKVLDRKSMGEDLFWAIRGGGGENFGIIAAWKIKLVAVPSKS<br>TIFSVKKNMEIHGLVKLFNKWQNIAYKYDKDLVLMTHFITKNITDNHGKNKT<br>TVHGYFSSIFHGGVDSLVDLMNKSFPELGIKKTDCKEFSWIDTTIFYSGVV<br>NFNTANFKKEILLDRSAGKKTAFSIKLDYVKKPIPETAMVKILEKLYEEDVG<br>AGMYVLYPYGGIMEEISESAIPFPHRAGIMYELWYTASWEKQEDNEKHIN<br>WVRSVYNFTTPYVSQNPRLAYLNYRDLDLGKTNHASPNNYTQARIWGEK<br>YFGKNFNRLVKVKTKVDPNNFFRNEQSIPPLPPHHH* |
| 3 | Nucleotide Sequence of Paralog "007396F" THCA Synthase | ATGAATTGCTCAACATTCTCCTTTTGGTTTGTTTGCAAAATAATATTTTT<br>CTTTCTCTCATTCAATATCCAAATTTCAATAGCTAATCCTCAAGAAAACT<br>TCCTTAAATGCTTCTCGGAATATATTCCTAACAATCCAGCAAATCCAAA<br>ATTCATATACACTCAACACGACCAATTGTATATGTCTGTCCTGAATTCG<br>ACAATACAAAATCTTAGATTCACCTCTGATACAACCCCAAAACCACTCG<br>TTATTGTCACTCCTTCAAATGTCTCCCATATCCAGGCCAGTATTCTCTG<br>CTCCAAGAAAGTTGGTTTGCAGATTCGAACTCGAAGCGGTGGCCATG<br>ATGCTGAGGGTTTGTCCTACATATCTCAAGTCCCATTTGCTATAGTAGA<br>CTTGAGAAACATGCATACGGTCAAAGTAGATATTCATAGCCAAACTGC<br>GTGGGTTGAAGCCGGAGCTACCCTTGGAGAAGTTTATTATTGGATCAA<br>TGAGATGAATGAGAATTTTAGTTTTCCTGGTGGGTATTGCCCTACTGTT<br>GGCGTAGGTGGACACTTTAGTGGAGGAGGCTATGGAGCATTGATGCG<br>AAATTATGGCCTTGCGGCTGATAATATCATTGATGCACACTTAGTCAAT<br>GTTGATGGAAAAGTTCTAGATCGAAAATCCATGGGAGAAGATCTATTTT<br>GGGCTATACGTGGTGGAGGAGGAGAAAACTTTGTAATCATTGCAGCAT<br>GGAAAATCAAACTTGTTGTTGTCCCATCAAAGGCTACTATATTGAGTGT<br>TAAAAAGAACATGGAGATACATGGGCTTGTCAAGTTATTTAACAAATGG<br>CAAAATATTGCTTACAAGTATGACAAAGATTTAATGCTCACGACTCACT<br>TCAGAACTAGGAATATTACAGATAATCATGGGAAGAATAAGACTACAG<br>TACATGGTTACTTCTCTTCCATTTTTCTTGGTGGAGTGGATAGTCTAGT<br>TGACTTGATGAACAAGAGCTTTCCTGAGTTGGGTATTAAAAAAACTGAT<br>TGCAAAGAATTGAGCTGGATTGATACAACCATCTTCTACAGTGGTGTT<br>GTAAATTACAACACTGCTAATTTTAAAAAGGAAATTTTGCTTGATAGAT<br>CAGCTGGGAAGAAGACGGCTTTCTCAATTAAGTTAGACTATGTTAAGA<br>AACTAATACCTGAAACTGCAATGGTCAAAATTTTGGAAAAATTATATGA<br>AGAAGAGGTAGGAGTTGGGATGTATGTTGTACCCTTACGGTGGTAT<br>AATGGATGAGATTTCAGAATCAGCAATTCCATTCCCTCATCGAGCTGG<br>AATAATGTATGAACTTTGGTACACTGCTACCTGGGAGAAGCAAGAAGA<br>TAACGAAAAGCATATAAACTGGGTTCGAAGTGTTTATAATTTCACAACT<br>CCTTATGTGTCCCAAAATCCAAGATTGGCGTATCTCAATTATAGGGAC<br>CTTGATTTAGGAAAAACTAATCCTGAGAGTCCTAATAATTACACACAAG<br>CACGTATTTGGGGTGAAAAGTATTTTGGTAAAAATTTTAACAGGTTAGT<br>TAAGGTGAAAACCAAAGCTGATCCCAATAATTTTTTTAGAAACGAACAA<br>AGTATCCCACCTCTTCCACCGCGTCATCATTAA |
| 4 | Amino Acid Sequence of Paralog "007396F" THCA Synthase | MNCSTFSFWFVCKIIFFFLSFNIQISIANPQENFLKCFSEYIPNNPANPKFIY<br>TQHDQLYMSVLNSTIQNLRFTSDTTPKPLVIVTPSNVSHIQASILCSKKVGL<br>QIRTRSGGHDAEGLSYISQVPFAIVDLRNMHTVKVDIHSQTAWVEAGATL<br>GEVYYWINEMNENFSFPGGYCPTVGVGGHFSGGGYGALMRNYGLAAD<br>NIIDAHLVNVDGKVLDRKSMGEDLFWAIRGGGGENFVIIAAWKIKLVVVPS<br>KATIFSVKKNMEIHGLVKLFNKWQNIAYKYDKDLMLTTHFRTRNITDNHGK<br>NKTTVHGYFSSIFLGGVDSLVDLMNKSFPELGIKKTDCKELSWIDTTIFYS<br>GVVNYNTANFKKEILLDRSAGKKTAFSIKLDYVKKLIPETAMVKILEKLYEE<br>EVGVGMYVLYPYGGIMDEISESAIPFPHRAGIMYELWYTATWEKQEDNEK<br>HINWVRSVYNFTTPYVSQNPRLAYLNYRDLDLGKTNPESPNNYTQARIW<br>GEKYFGKNFNRLVKVKTKADPNNFFRNEQSIPPLPPRHH* |
| 5 | Nucleotide Sequence of Paralog "006591F" CBDA Synthase | ATGAAGTACTCAACATTCTGTTTTTGGTATGTTTGCAAGATAATATTTTT<br>CTTTCTCTCATTCAATATCCAAATTTCAATAGCTAATCCTCAAGAAAACT<br>TCCTTAAATGCTTCTCACAATATATTCCCACCAATGTAACAAATGCAAA<br>ACTCGTATACACTCAACACGACCAATTTTATATGTCTATCCTAAATTCG<br>ACCATACAAAATCTTAGATTTACCTCTGACACAACCCCAAAACCACTTG<br>TTATCATCACTCCTTTAAATGTCTCCCATATCCAGGCACTATTCTATG<br>CTCCAAGAAAGTTGGCTTGCAGATTCGAACTCGAAGCGGTGGTCATG |

| SEQ ID NO | Description | Sequence |
|---|---|---|
| | | ATGCTGAGGGCATGTCCTACATATCTCAAGTCCCATTTGTTATAGTAGA<br>CTTGAGAAACATGCATTCGGTCAAAATAGATGTTCATAGCCAAACTGC<br>ATGGGTTGAAGCCGGAGCTACCCTTGGAGAAGTTTATTATTGGATCAA<br>TGAGAACAATGAGAATCTTAGTTTTCCTGCTGGGTACTGCCCTACTGT<br>TGGCGCGGGTGGACACTTTAGTGGAGGAGGCTATGGAGCATTGATGC<br>GAAATTATGGCCTCGCGGCTGATAATATCATTGATGCGCACTTAGTCA<br>ATGTTGATGGAAAAGTTTTAGATCGAAATCCATGGGGAAGATTTGT<br>TTTGGGCTATACGTGGTGGTGGAGGAGAAAACTTTGGAATCATTGCAG<br>CGTGGAAAATTAGACTTGTTGCTGTCCCATCAATGTCTACTATATTCAG<br>TGTTAAAAAGAACATGGAGATACATGAGCTTGTCAAGTTAGTTAACAAA<br>TGGCAAAATATTGCTTACATGTATGAAAAGAATTATTACTCTTTACTCA<br>CTTTATAACCAGGAATATTACAGATAATCAAGGGAAGAATAAGACAACA<br>ATACACAGTTACTTCTCCTCCATTTTCCATGGTGGAGTGGATAGTCTAG<br>TCGACTTGATGAACAAGAGCTTTCCTGAATTGGGTATTAAAAAAACAGA<br>TTGCAAACAGTTGAGCTGGATTGATACTATCATCTTCTACAGTGGTCTT<br>GTAAATTACAACACAACTAATTTTAAAAAAGAAATTTTGCTTGATAGATC<br>AGGTGGGCGGAAGGCGGCTTTCTCGATTAAGTTAGACTATGTTAAGAA<br>ACCGATTCCAGAAACCGCAATGGTCACAATTTTGGAAAAATTATATGAA<br>GAAGATGTAGGAGTTGGGATGTTTGTGTTTTACCCTTATGGTGGTATA<br>ATGGATGAGATTTCAGAATCAGCAATTCCATTCCCTCATCGAGCTGGA<br>ATCATGTATGAAATTTGGTACATAGCTTCATGGGAGAAGCAAGAAGAT<br>AATGAAAAGCATATAAACTGGATTCGGAATGTTTATAATTTCACGACTC<br>CTTATGTGTCCCAAAATCCAAGAATGGCGTATCTCAATTATAGGGACC<br>TTGATTTAGGAAAAACTAATTTCGAGACTCCTAATAATTACACACAAGC<br>ACGTATTTGGGGTGAAAAGTATTTTGGTAAAAATTTTAATAGGTTAGTA<br>AAAGTAAAAACCAAGGTTGATCCCGATAATTTCTTTAGAAACGAACAAA<br>GCATCCCACCTCTTCCCCTACGTCATCATTAA |
| 6 | Amino Acid Sequence of Paralog "006591F" CBDA Synthase | MKYSTFCFWYVCKIIFFFLSFNIQISIANPQENFLKCFSQYIPTNVTNAKLVY<br>TQHDQFYMSILNSTIQNLRFTSDTTPKPLVIITPLNVSHIQGTILCSKKVGLQ<br>IRTRSGGHDAEGMSYISQVPFVIVDLRNMHSVKIDVHSQTAWVEAGATLG<br>EVYYWINENNENLSFPAGYCPTVGAGGHFSGGGYGALMRNYGLAADNII<br>DAHLVNVDGKVLDRKSMGEDLFWAIRGGGGENFGIIAAWKIRLVAVPSMS<br>TIFSVKKNMEIHELVKLVNKWQNIAYMYEKELLLFTHFITRNITDNQGKNKT<br>TIHSYFSSIFHGGVDSLVDLMNKSFPELGIKKTDCKQLSWIDTIIFYSGLVN<br>YNTTNFKKEILLDRSGGRKAAFSIKLDYVKKPIPETAMVTILEKLYEEDVGV<br>GMFVFYPYGGIMDEISESAIPFPHRAGIMYEIWYIASWEKQEDNEKHINWI<br>RNVYNFTTPYVSQNPRMAYLNYRDLDLGKTNFESPNNYTQARIWGEKYF<br>GKNFNRLVKVKTKVDPDNFFRNEQSIPPLPLRHH* |
| 7 | Nucleotide Sequence of Paralog "005134F" CBDA Synthase | ATGAAGTACTCAACATTCTGTTTTTGGTATGTTTGCAAGATAATATTTTT<br>CTTTCTCTCATTCAATATCCAAATTTCAATAGCTAATCCTCAAGAAAACT<br>TCCTTAAATGCTTCTCACAATATATTCCCACCAATGTAACAAATGCAAA<br>ACTGGTATACAGTCAACACGACCAATTTTATATGTCTATCCTAAATTCG<br>ACCATACAAAATCTTAGATTTACCTCTGAAACAACCCCAAAACCACTTG<br>TTATCATCACTCCTTTAAATGTCTCCCATATCCAAGGCACTATTCTATG<br>CTCCAAGAAAGTTGGCTTGCAGATTCGAACTCGAAGCGGTGGTCATG<br>ATGCTGAGGGCATGTCCTACATATCTGAAGTCCCATTTGTTATAGTAG<br>ACTTGAGAAACATGCATTCGGTCAAAATAGATGTTCATAGCCAAACTG<br>CATGGGTTGAAGCCGGAGCTACCCTTGGAGAAGTTTATTATTGGATCA<br>ATGAGAACAATGAGAATCTTAGTTTTCCTGCTGGGTACTGCCCTACTG<br>TTGGCGCGGGTGGACACTTTAGTGGAGGAGGCTATGGAGCATTGATG<br>CGAAATTATGGCCTCGCGGCTGATAATATCATTGATGCGCACTTAGTC<br>AATGTTGATGGAAAAGTTTTAGATCGAAATCCATGGGGAAGATTTG<br>TTTTGGGCTATACGTGGTGGTGGAGGAGAAAACTTTGGAATCATTGCA<br>GCGTGGAAAATTAGACTTGTTGCTGTCCCATCAATGTCTACTATATTCA<br>GTGTTAAAAAGAACATGGAGATACATGAGCTTGTCAAGTTAGTTAACAA<br>ATGGCAAAATATTGCTTACATGTATGAAAAGAATTATTACTCTTTACTC<br>ACTTTATAACCAGGAATATTACAGATAATCAAGGGAAGAATAAGACAAC<br>AATACACAGTTACTTCTCCTCCATTTTCCATGGTGGAGTGGATAGTCTA<br>GTCGACTTGATGAACAAGAGCTTTCCTGAATTGGGTATTAAAAAAACA<br>GATTGCAAACAGTTGAGCTGGATTGATACTATCATCTTCTACAGTGGT<br>GTTGTAAATTACAACACAACTAATTTTAAAAAAGAAATTTTGCTTGATAG<br>ATCAGGTGGGCGGAAGGCGGCTTTCTCGATTAAGTTAGACTATGTTAA<br>GAAACCGATTCCAGAAACCGCAATGGTCACAATTTTGGAAAAATTATAT<br>GAAGAAGATGTAGGAGTTGGGATGTTTGTGTTTTACCCTTATGGTGGT<br>ATAATGGATGAGATTTCAGAATCAGCAATTCCATTCCCTCATCGAGCT<br>GGAATCATGTATGAAATTTGGTACATAGCTTCATGGGAGAAGCAAGAA<br>GATAATGAAAAGCATATAAACTGGATTCGGAATGTTTATAATTTCACGA<br>CTCCTTATGTGTCCCAAAATCCAAGAATGGCGTATCTCAATTATAGGG<br>ACCTTGATTTAGGAAAAACTAATTTCGAGAGTCCTAATAATTACACACA<br>AGCACGTATTTGGGGTGAAAAGTATTTTGGTAAAAATTTTAATAGGTTA<br>GTAAAAGTAAAAACCAAGGTTGATCCCGATAATTTCTTTAGAAACGAAC<br>AAAGCATCCCACCTCTTCCCCTACGTCATCATTAA |

| SEQ ID NO | Description | Sequence |
|---|---|---|
| 8 | Amino Acid Sequence of Paralog "005134F" CBDA Synthase | MKYSTFCFWYVCKIIFFFLSFNIQISIANPQENFLKCFSQYIPTNVTNAKLVY SQHDQFYMSILNSTIQNLRFTSETTPKPLVIITPLNVSHIQGTILCSKKVGLQ IRTRSGGHDAEGMSYISEVPFVIVDLRNMHSVKIDVHSQTAWVEAGATLG EVYYWINENNENLSFPAGYCPTVGAGGHFSGGGYGALMRNYGLAADNII DAHLVNVDGKVLDRKSMGEDLFWAIRGGGGENFGIIAAWKIRLVAVPSMS TIFSVKKNMEIHELVKLVNKWQNIAYMYEKELLLFTHFITRNITDNQGKNKT TIHSYFSSIFHGGVDSLVDLMNKSFPELGIKKTDCKQLSWIDTIIFYSGVVN YNTTNFKKEILLDRSGGRKAAFSIKLDYVKKPIPETAMVTILEKLYEEDVGV GMFVFYPYGGIMDEISESAIPFPHRAGIMYEIWYIASWEKQEDNEKHINWI RNVYNFTTPYVSQNPRMAYLNYRDLDLGKTNFESPNNYTQARIWGEKYF GKNFNRLVKVKTKVDPDNFFRNEQSIPPLPLRHH* |
| 9 | Nucleotide Sequence of Paralog "004341F" CBDA Synthase | ATGAAGTACTCAACATTCTGTTTTTGGTATGTTTGCAAGATAATATTTTT CTTTCTCTCATTCAATATCCAAATTTCAATAGCTAATCCTCAAGAAAACT TCCTTAAATGCTTCTCACAATATATTCCCACCAATGTAACAAATGCAAA ACTCGTATACACTCAACACGACCAATTTTATATGTCTATCCTAAATTCG ACCATACAAAATCTTAGATTTACCTCTGACACAACCCCAAAACCACTTG TTATCATCACTCCTTTAAATGTCTCCCATATCCAAGGCACTATTCTATG CTCCAAGAAAGTTGGCTTGCAGATTCGAACTCGAAGCGGTGGTCATG ATGCTGAGGGCATGTCCTACATATCTCAAGTCCCATTTGTTATAGTAGA CTTGAGAAACATGCATTCGGTCAAAATAGATGTTCATAGCCAAACTGC ATGGGTTGAAGCCGGAGCTACCCTTGGAGAAGTTTATTATTGGATCAA TGAGAACAATGAGAATCTTAGTTTTCCTGCTGGGTACTGCCCTACTGT TGGCGCGGGTGGACACTTTAGTGGAGGAGGCTATGGAGCATTGATGC GAAATTATGGCCTCGCGGCTGATAATATCATTGATGCGCACTTAGTCA ATGTTGATGGAAAAGTTTTAGATCGAAAATCCATGGGGGAAGATTTGT TTTGGGCTATACGTGGTGGTGGAGGAGAAAACTTTGGAATCATTGCAG CGTGGAAAATTAGACTTGTTGCTGTCCCATCAATGTCTACTATATTCAG TGTTAAAAAGAACATGGAGATACATGAGCTTGTCAAGTTAGTTAACAAA TGGCAAAATATTGCTTACATGTATGAAAAAGAATTATTACTCTTTACTCA CTTTATAACCAGGAATATTACAGATAATCAAGGGAAGAATAAGACAACA ATACACAGTTACTTCTCCTCCATTTTCCATGGTGGAGTGGATAGTCTAG TCGACTTGATGAACAAGAGCTTTCCTGAATTGGGTATTAAAAAAACAGA TTGCAAACAGTTGAGCTGGATTGATACTATCATCTTCTACAGTGGTCTT GTAAATTACAACACTACTAATTTTAAAAAAGAAATTTTGCTTGATAGATC AGGTGGGCGGAAGGCGGCTTTCTCGATTAAGTTAGACTATGTTAAGAA ACCGATTCCAGAAACCGCAATGGTCACAATTTTGGAAAAATTATATGAA GAAGATGTAGGAGTTCGGATGTTTGTTTTTACCCTTATGGTGGTATA ATGGATGAGATTTCAGAATCAGCAATTCCATTCCCTCATCGAGCTGGA ATCATGTATGAAATTTGGTACATAGCTTCATGGGAGAAGCAAGAAGAT AATGAAAAGCATATAAACTGGATTCGGAATGTTTATAATTTCACGACTC CTTATGTGTCCCAAAATCCAAGAATGGCGTATCTCAATTATAGGGACC TTGATTTAGGAAAAACTAATTTTGAGAGTCCTAATAATTACACACAAGC ACGTATTTGGGGTGAAAAGTATTTTGGTAAAAATTTTAATAGGTTAGTA AAAGTAAAAACCAAGGTTGATCCCGATAATTTCTTTAGAAACGAACAAA GCATCCCACCTCTTCCCCTGCGTCATCATTAA |
| 10 | Amino Acid Sequence of Paralog "004341F" CBDA Synthase | MKYSTFCFWYVCKIIFFFLSFNIQISIANPQENFLKCFSQYIPTNVTNAKLVY TQHDQFYMSILNSTIQNLRFTSDTTPKPLVIITPLNVSHIQGTILCSKKVGLQ IRTRSGGHDAEGMSYISQVPFVIVDLRNMHSVKIDVHSQTAWVEAGATLG EVYYWINENNENLSFPAGYCPTVGAGGHFSGGGYGALMRNYGLAADNII DAHLVNVDGKVLDRKSMGEDLFWAIRGGGGENFGIIAAWKIRLVAVPSMS TIFSVKKNMEIHELVKLVNKWQNIAYMYEKELLLFTHFITRNITDNQGKNKT TIHSYFSSIFHGGVDSLVDLMNKSFPELGIKKTDCKQLSWIDTIIFYSGLVN YNTTNFKKEILLDRSGGRKAAFSIKLDYVKKPIPETAMVTILEKLYEEDVGV GMFVFYPYGGIMDEISESAIPFPHRAGIMYEIWYIASWEKQEDNEKHINWI RNVYNFTTPYVSQNPRMAYLNYRDLDLGKTNFESPNNYTQARIWGEKYF GKNFNRLVKVKTKVDPDNFFRNEQSIPPLPLRHH* |
| 11 | Nucleotide Sequence of Paralog "006705F" THCA Synthase | ATGAATTGCTCAACATTCTCCTTTTGGTTTGTTTGCAAAATAATATTTTT CTTTCTCTCATTCAATATCCAAATTTCAATAGCTAATCCTCAAGAAAACT TCCTTAAATGCTTCTCGGAATATATTCCTAACAATCCAGCAAATCCAAA ATTCATATACACTCAACACGACCAATTGTATATGTCTGTCCTGAATTCG ACAATACAAAATCTTAGATTCACCTCTGATACAACCCCAAAACCACTTG TTATTGTCACTCCTTCAAATGTCTCCCATATCCAGGCCAGTATTCTCTG CTCCAAGAAAGTTGGTTTGCAGATTCGAACTCGAAGCGGTGGCCATG ATGCTGAGGGTTTGTCCTACATATCTCAAGTCCCATTTGCTATAGTAGA CTTGAGAAACATGCATACGGTCAAAGTAGATATTCATAGCCAAACTGC GTGGGTTGAAGCCGGAGCTACCCTTGGAGAAGTTTATTATTGGATCAA TGAGATGAATGAGAATTTTAGTTTTCCTGGTGGGTATTGCCCTACTGTT GGCGTAGGTGGACACTTTAGTGGAGGAGGCTATGGAGCATTGATGCG AAATTATGGCCTTGCGGCTGATAATATCATTGATGCACACTTAGTCAAT GTTGATGGAAAAGTTCTAGATCGAAAATCCATGGGAGAAGATCTATTTT GGGCTATACGTGGTGGAGGAGGAGAAAACTTTGGAATCATTGCAGCA TGGAAAATCAAACTTGTTGTTGTCCCATGAAAGGCTACTATATTCAGTG |

| SEQ ID NO | Description | Sequence |
|---|---|---|
| | | TTAAAAAGAACATGGAGATACATGGGCTTGTCAAGTTATTTAACAAATG<br>GCAAAATATTGCTTACAAGTATGACAAAGATTTAATGCTCACGACTCAC<br>TTCAGAACTAGGAATATTACAGATAATCATGGGAAGAATAAGACTACA<br>GTACATGGTTACTTCTCTTCCATTTTTCTTGGTGGAGTGGATAGTCTAG<br>TTGACTTGATGAACAAGAGCTTTCCTGAGTTGGGTATTAAAAAAACTGA<br>TTGCAAAGAATTGAGCTGGATTGATACAACCATCTTCTACAGTGGTGTT<br>GTAAATTACAACACTGCTAATTTTAAAAAGGAAATTTTGCTTGATAGAT<br>CAGCTGGGAAGAAGACGGCTTTCTCAATTAAGTTAGACTATGTTAAGA<br>AACTAATACCTGAAACTGCAATGGTCAAAATTTTGGAAAAATTATATGA<br>AGAAGAGGTAGGAGTTGGGATGTATGTGTTGTACCCTTACGGTGGTAT<br>AATGGATGAGATTTCAGAATCAGCAATTCCATTCCCTCATCGAGCTGG<br>AATAATGTATGAACTTTGGTACACTGCTACCTGGGAGAAGCAAGAAGA<br>TAACGAAAAGCATATAAACTGGGTTCGAAGTGTTTATAATTTCACAACT<br>CCTTATGTGTCCCAAAATCCAAGATTGGCGTATCTCAATTATAGGGAC<br>CTTGATTTAGGAAAAACTAATCCTGAGAGTCCTAATAATTACACACAAG<br>CACGTATTTGGGGTGAAAAGTATTTTGGTAAAAATTTTAACAGGTTAGT<br>TAAGGTGAAAACCAAAGCTGATCCCAATAATTTTTTTAGAAACGAACAA<br>AGTATCCCACCTCTTCCACCGCGTCATCATTAA |
| 12 | Amino Acid Sequence of Paralog "006705F" THCA Synthase | MNCSTFSFWFVCKIIFFFLSFNIQISIANPQENFLKCFSEYIPNNPANPKFIY<br>TQHDQLYMSVLNSTIQNLRFTSDTTPKPLVIVTPSNVSHIQASILCSKKVGL<br>QIRTRSGGHDAEGLSYISQVPFAIVDLRNMHTVKVDIHSQTAWVEAGATL<br>GEVYYWINEMNENFSFPGGYCPTVGVGGHFSGGGYGALMRNYGLAAD<br>NIIDAHLVNVDGKVLDRKSMGEDLFWAIRGGGGENFGIIAAWKIKLVVVPS<br>KATIFSVKKNMEIHGLVKLFNKWQNIAYKYDKDLMLTTHFRTRNITDNHGK<br>NKTTVHGYFSSIFLGGVDSLVDLMNKSFPELGIKKTDCKELSWIDTTIFYS<br>GVVNYNTANFKKEILLDRSAGKKTAFSIKLDYVKKLIPETAMVKILEKLYEE<br>EVGVGMYVLYPYGGIMDEISESAIPFPHRAGIMYELWYTATWEKQEDNEK<br>HINWVRSVYNFTTPYVSQNPRLAYLNYRDLDLGKTNPESPNNYTQARIW<br>GEKYFGKNFNRLVKVKTKADPNNFFRNEQSIPPLPPRHH* |
| 13 | c395 Forward PCR Primer | TCACCTCTAACACAACCCCAAAA |
| 14 | c395 Reverse PCR Primer | CCAAAAGAGATCTTCCCCCATA |
| 15 | c8242 Forward PCR Primer | GCGTTGTACCCTTACGGTTG |
| 16 | c8242 Reverse PCR Primer | TTTTGACTCTTGGGATCATTTATTC |

The present invention relates to compositions and methods for providing desired cannabinoid production in plants. More particularly, the invention relates to compositions and methods for using genetic analysis for breeding *cannabis* plants, including but not limited to cultivars, varieties, lines, and methods of breeding the same for commercial use, the breeding methods further involving identifying and using genetic markers for cannabinoid compound production traits.

Advantages of growing and using a *cannabis* plant that produces a known or desired cannabinoid or combination of cannabinoids includes consistent and predictable therapeutic effect resulting from ingestion of the plant materials. The potential market is substantial because of the recent understanding of medicinal effects of certain cannabinoids and cannabinoid combinations.

The inventors have analyzed the cannabinoid synthase genes from the gene structure of many *cannabis* plant varieties and compared to computationally folded enzyme structure to better understand the complex mechanism of cannabinoid production. With a better understanding of the mechanism controlling this secondary metabolite production, more accurate breeding of *cannabis* plant varieties may be conducted for species specific for cannabinoid synthase genes of interest, which control the upstream processes compared to the conversion of CBGA to THCA/CBDA.

*Cannabis*, an angiosperm from the family cannabacea that has been cultivated for thousands of years for multiple purposes, particularly due to the production of secondary metabolites known as cannabinoids. Hundreds of varieties of cannabis have been bred and identified, most of which differ in the content of the two most well-known cannabinoids; delta-9-tetrahydrocannabinolic acid (THCA) and Cannabidolic acid (CBDA) in the plant.

The methods of the present invention are not limited to the use of any particular plant. Indeed, a variety of plants are contemplated for introducing CBDA and/or THCA content.

The present invention relates to compositions and methods for identifying and providing CBDA and/or THCA content in a plant. More particularly, the invention relates to compositions and methods for using cannabinoid synthase paralogs for breeding *cannabis* plants that produce a desired amount or ratio of cannabinoid(s), including but not limited to cultivars, varieties, lines and methods of breeding the same for commercial use, the breeding methods further involving identifying and using genetic markers for specific cannabinoid synthase paralogs.

Specifically, this invention discloses novel PCR primers/probes that identify specific cannabinoid synthase paralogs related to CBDA production in cannabis plants.

In experiments conducted during the course of the present invention, sources and types of CBDA and THCA production were identified.

To develop the desired cannabis cultivars, sources of germplasm comprising cannabis synthase paralogs must be identified. In experiments conducted during the course of the present invention, the relationship between the occurrence of cannabinoid synthase paralog type and copy number with cannabinoid content in many known cannabis varieties were established.

The present invention contemplates providing lines of specifically bred cannabis plants by crossbreeding cannabis cultivars that have been identified by the presence or copy number of specific cannabinoid synthase paralogs using the PCR primers/probes of this disclosure.

The present invention contemplates the use of transgenic plants comprising a heterologous transgene encoding a cannabinoid synthase paralog identified using the PCR primers/probes of this disclosure.

Another aspect of the present invention is to provide high content CBDA producing *cannabis* plants by crossbreeding *cannabis* cultivars having specific cannabinoid synthase paralogs identified using the PCR primers/probes of this disclosure.

Another aspect of the present invention is to provide low content CBDA producing *cannabis* plants by crossbreeding *cannabis* cultivars having specific cannabinoid synthase paralogs identified using the PCR primers/probes of this disclosure.

Another aspect of the invention relates to the cloning and expression of the cannabinoid synthase enzymes encoded by the paralogs identified in this disclosure, that play a role in the biosynthesis of cannabinoids. This aspect may also include the use of a eukaryotic expression system for the manufacture of cannabinoids and cannabinoid analogs using these recombinant synthase enzymes.

In these aspects, the cannabinoid synthase enzymes may be encoded by the cannabinoid synthase paralogs of this disclosure, including specifically the THCA synthases designated "001774F" (SEQ ID NO:1); "007396F" (SEQ ID NO:3); and "006705F" (SEQ ID NO: 1) and the CBDA synthases designated "006591 F" (SEQ ID NO:5); "005134F" (SEQ ID NO:7); "004341 F" (SEQ ID NO:9). These synthase enzymes may be used in the production of recombinant cannabinoid synthase enzymes, and/or the production of synthetic cannabinoid compounds.

Exemplary eukaryotic cells suitable for cloning and expression of the cannabinoid synthase enzymes include, without limitation, *E coli*, yeast and baculovirus hosts. An embodiment of this technology is a method for the large-scale production of several cannabinoid synthase enzymes including tetrahydrocannabinolic acid synthase (THCA synthase) and cannabidiolic acid synthase (CBDA synthase) using a *Pichia* yeast expression system. Accordingly, the production of these recombinant enzymes can be carried out by transforming yeast with a DNA construct that comprises a gene encoding one or more of the cannabinoid synthase paralogs identified in this disclosure for THCA synthase or CBDA synthase, and culturing the transformed yeast cells under conditions suitable for promoting the expression of a functionally active enzyme. The recombinant enzyme may then be recovered from the transformed cells gown in culture by lysing and isolating the recombinant synthase enzymes, or from the fermentation media where those recombinantly produced synthase enzymes are secreted into the growth media.

A related aspect of the present invention provides methods and systems for producing cannabinoids or cannabinoid analogs. Such methods may include the use of a fermentor holding a medium and a plurality of cells, wherein the cells are recombinantly modified to express a cannabinoid synthase enzyme and produce the desired cannabinoids in vitro. The cannabinoid compounds may then be recovered from the recombinant organisms or from the growth media.

Thus, the polynucleotides encoding the cannabinoid synthase paralogs of this disclosure may be used in methods of plant breeding, mutagenesis or genetic engineering, as well as methods for making recombinant cells, and recombinant organisms such as recombinant plants such as *cannabis* plants with enhanced THCA and/or CBDA synthase activity, and/or enhanced THCA and/or CBDA content, as well as cell free systems. Such systems and methods are known and described in detail in PCT patent application No. PCT/CA2015/000423, filed 29 Jun. 2015, which is incorporated herein by reference in its entirety, and in U.S. Pat. No. 9,359,625, issued 7 Jun. 2016, which is incorporated herein by reference in its entirety.

Furthermore, methods of inactivating or silencing the cannabinoid synthase paralogs of this disclosure in a *cannabis* cell and/or plant are contemplated, for example, to block and/or reduce cannabinoid biosynthesis and the cannabinoid content of a *cannabis* cell or plant Such methods may be used, for example, to block or reduce the production of THCA THCA and/or CBDA, and/or to increase the production of CBGA.

Thus, an embodiment of this disclosure provides a nucleic acid molecule comprising a nucleotide sequence having at least about 95% sequence identity to cannabinoid synthase paralogs of this disclosure, including specifically the THCA synthases designated "001774F" (SEQ ID NO:1); "007396F" (SEQ ID NO:3); and "006705F" (SEQ ID NO:11), and the CBDA synthases designated "006591F" (SEQ ID NO:5); "005134F" (SEQ ID NO:7); and "004341F" (SEQ ID NO:9), or the complement thereof, that encodes a polypeptide having cannabinoid synthase activity; operably linked to a heterologous nucleic acid sequence suitable for expression in a cell or organism. In these embodiments, the encoded polypeptide may demonstrate THCA synthase enzymatic activity or CBDA synthase enzymatic activity.

It will be appreciated that this disclosure embraces the degeneracy of codon usage as would be understood by one of ordinary skill in the art and as illustrated in the Table of Codon Degeneracies.

| Table of Codon Degeneracies | |
|---|---|
| Amino Acid | Codons |
| Ala/A | GCT, GCC, GCA, COG |
| Arg/R | CGT, CCC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |

-continued

Table of Codon Degeneracies

| Amino Acid | Codons |
|---|---|
| Met/M | ATG |
| Phe/F | TTT, TTC |
| Pro/P | CCT, CCC, CCA, CCG |
| Ser/S | TCT, TCC, TCA, TCG, ACT, AGC |
| Thr/T | ACT, ACC, ACA, ACG |
| Trp/W | TGG |
| Tyr/Y | TAT, TAC |
| Val/V | GTT, CTC, GTA, CTC |
| START | ATG |
| STOP | TAG, TGA, TAA |

Furthermore, it will be understood by one skilled in the art that conservative substitutions may be made in the amino acid sequence of a polypeptide without disrupting the structure or function of the polypeptide. Conservative amino acid substitutions are accomplished by the skilled artisan by substituting amino acids with similar hydrophobicity, polarity, and R-chain length for one another. Additionally, by comparing aligned sequences of homologous proteins from different species, conservative amino acid substitutions may be identified by locating amino acid residues that have been mutated between species without altering the basic functions of the encoded proteins. The following table provides an exemplary list of conservative substitutions.

Table of Conservative Substitutions

| Type of Amino Acid | Substitutable Amino Acids |
|---|---|
| Hydrophilic: | Ala, Pro, Gly, Glu, Asp, Gln, Asn, Ser, Thr |
| Sulphydryl: | Cys |
| Aliphatic: | Val, Ile, Leu, Met |
| Basic: | Lys, Arg, His |
| Aromatic: | Phe, Tyr, Trp |

A related aspect of this disclosure therefore includes a cell or organism comprising a nucleic acid comprising a nucleotide sequence having at least about 95% sequence identity to cannabinoid synthase paralogs of this disclosure, including specifically the THCA synthases designated "001774F" (SEQ ID NO:1); "007396F" (SEQ ID NO:3); and "006705F" (SEQ ID NO:11), and the CBDA synthases designated "006591F" (SEQ ID NO:5); "005134F" (SEQ ID NO:7); and "004341F" (SEQ ID NO:9), or the complement thereof, that encodes a polypeptide having cannabinoid synthase activity; operably linked to a heterologous nucleic acid sequence suitable for expression in the cell or organism, such that the cell or organism expresses a recombinant cannabinoid synthase. In these embodiments, the expressed polypeptide may demonstrate THCA synthase enzymatic activity or CBDA synthase enzymatic activity.

In a related aspect, this disclosure includes a culture supernatant of a recombinant organism culture, for example a recombinant yeast cell culture wherein the recombinantly produced cannabinoid synthase and/or cannabinoid is secreted into the culture supernatant.

In a related aspect, this disclosure includes an expression vector that may be used to transfer a nucleic acid encoding a cannabinoid synthase paralog of this disclosure into a host cell. Such expression vectors may include cosmids, plasmids, or modified viruses (e.g. replication defective retroviruses, adenoviruses and adeno-associated viruses), so long as the vector is compatible with the host cell used. The expression vectors are suitable for transformation of a host cell if they contain a nucleic acid molecule of this disclosure and regulatory sequences selected on the basis of the host cells to be used for expression, which is/are operatively linked to the nucleic acid molecule encoding the cannabinoid synthase, to allows expression of the nucleic acid. These vectors may be used to create transgenic or recombinant organisms or recombinant cells (e.g. optionally cells of recombinant organisms) that produce recombinant cannabinoid synthases with THCA or CBDA synthase enzymatic activity. Preferably, the recombinant organism is a recombinant plant, recombinant multicellular microorganism or recombinant insect. Plants are preferably of the genus Cannabis, for example Cannabis sativa L, Cannabis indica Lam. and Cannabis ruderalis Janisch, especially Cannabis sativa. Microorganisms are preferably bacteria (e.g. Escherichia coli) or yeast (e.g. Saccharomyces cerevisiae, Pichia pastoris).

In all of these aspects, the nucleotide sequence encoding the cannabinoid synthase paralogs of this disclosure may be codon optimized for expression in the cell or organism used in the recombinant production of the synthase enzyme and/or cannabinoid(s).

The following Examples are illustrative and should not be interpreted in any way to limit the scope of the invention.

EXAMPLES

High-throughput screening methods have been developed for botanical applications to assist breeders select for traits, such as the chemical biosynthesis and other phenotypic traits in numerous plant industries. The marker system developed by the inventors and disclosed herein is specific to the Cannabis genus and allows one to identify and screen for potential drug-producing cultivars. The inventors have identified informative regions of the cannabinoid synthase gene family and informative SNPs within those regions that have been targeted by novel markers, c395 and c8242. Furthermore, they discovered other secondary markers in the genome that correlate to bioaccumulation of THCA or CBDA, that can be incorporated with other paralog markers to create a chemically informative barcode or fingerprint for each strain that can help to better classify and name Cannabis.

INTRODUCTION

Cannabis, an angiosperm of the family cannabacea (Soltis et al. 2005; Bell et al. 2010), has been cultivated for thousands of years for multiple purposes, especially its distinct production of pharmacologically-active secondary metabolites known as cannabinoids (Russo 2007). Cannabis cultivation is now a multibillion-dollar industry that primarily targets the two most well-known cannabinoids; delta-9-tetrahydrocannabinolic acid (THCA) and Cannabidolic acid (CBDA). THCA is most commonly associated with psychoactive effects (Russo and McParland 2003; ElSholy and Slade 2005; Radwan et al. 2008). CBDA has gained recent popularity for its proposed non-psychoactive medicinal uses and less restricted use in the United States (Russo 2011; Swift et al. 2013).

THCA and CBDA are the final products of a three-step biochemical pathway and are produced in the last step by the enzymes THCA and CBDA synthase (THCAS and CBDAS) respectively (Gagne et al. 2012; Page and Boubakir 2014; Vergara et al. in prep). A third compound, Cannabichromenic acid (CBCA) is also a final product in this pathway produced by CBCA synthase. The precursor molecule acted on by the three cannabinoid synthases, Cannabigerolic acid (CBGA), (Page and Boubakir 2014; Vergara et al. in prep), is found in low quantities in both the US (Vergara et al. 2017) and worldwide (Swift et al. 2013).

Duplication and deletion of genomic regions may result in gene copy number (CN) variation or paralogs, which has been shown to be common in plant genes related to stress or disease resistance (Delledonne et al. 1998; Gaines et al. 2010; Żmieńko et al. 2014). It has been proposed that the ecological function of cannabinoids is to protect the plant from external stressors (ie. UV light, herbivory, & pathogens) (Langenheim 1994; McPartland et al. 2000; Sirikantaramas et al. 2005), and the genes coding for these cannabinoid synthases are found in multiple, divergent paralogs (Onofri et al. 2015) that vary in CN and alleles between and within lineages (Vergara in prep.). An example of a particularly significant such variation is the preeminence of functionally-compromised CBDAS alleles among high-THCA cultivars (Vergara et al in prep; Onofri et al. 2015).

Complex traits such as cannabinoid content often consist of multiple loci that make it difficult to determine their location or copy number. Due to their sequence similarity determining their sequence is problematic (Vergara et al in prep). Therefore, we developed specific primers that amplify unique regions within the paralogs directly responsible for the production of cannabinoids. Additionally, we established the SNPs with the largest effect size in the amplified regions of the three paralogs and other possible SNPs throughout the whole genome that could influence cannabinoid bioaccumulation.

The following methods were used to conduct the experiments and analysis described in Examples 1-3, below:

Genomic Assembly:

The genomic assembly used to identify cannabinoid paralogs belonged to a Y-chromosome-bearing dioecious plant the high-THCA marijuana cultivar, Pineapple-Banana-Bubba-Kush (PBBK), to generate a de novo assembly (Genbank: GCA_002090435.1) using Pacific Biosciences (PacBio) RSII SMrT-LR sequencing and -HGap2 (v. January 2015) (Chin et. al., 2013) software, yielding 18,355 contigs with 72× coverage. This individual plant harbors at least 11 putative synthase paralogs, one with near-identity to the archetype THCAS and two to the archetype CBDAS but the latter both having truncated genes related to synthase. We identified an additional 20 loci encoding putative FAD-dependent, berberine-bridge-forming enzymes of the family to which all known cannabinoid synthases belong.

Plant Material & Chemical Profiling:

Extracted DNA from 31 Cannabis cultivars used for the analyses was donated to Kane Lab at the University of Colorado Boulder for genomic studies. The genomic DNA was extracted with Qiagen DNA Easy protocol per the manufacturer's instructions. Chemical profiling for each strain was performed by Steep Hill Laboratories (Berkley, Calif.). Dried mature female flower material was prepared and assayed for cannabinoids using HPLC-UV detection as described in (Vergara et al., 2017) with Shimadzu LC equipment. For each archetypal classification of Cannabis, we had a least one cultivar to represent the follow types: Type 1 (THCA dominant), Type 2 (Mixed ratio).

Primer Set Development for Synthase Paralogs:

The primer sets we developed (c395 and c8242) target two paralogs of suite of cannabinoid synthases that are associated with production of CBDA. These two paralogs are truncated in the high THCA-producing PBBK plant, but may be functional in high CBDA-producing cultivars. Due to the high-level of sequence similarity in this gene family, it was difficult to make specific primers that would target only a single paralog. However, we were able to design two primer sets that amplified the paralogs in scaffolds 000395F (MXDB010000395.1) and 008242F (MXDB010008229.1) in the PacBio assembly with the primer sets c395 and c8242, respectively. We used Primer3 software to design stable primers in non-conserved areas between the paralogs but within the coding region of the single-exon synthase paralogs (Untergrasser, 2012). The c395 primer set:

```
F:
                                     (SEQ ID NO: 13)
5' TCACCTCTAACACAACCCCAAAA 3'

R:
                                     (SEQ ID NO: 14)
5' CCAAAAGAGATCTTCCCCCATA 3'
``` amplified a specific 465 nt region of paralog 000395F in 15 unique cultivars using PCR program 1 (see Thermocycler Programs Table). However, the c395 reverse primer is non-specific due to the presence of a second binding site within the genome. The c8242 primer set:

```
F:
                                     (SEQ ID NO: 15)
5' GCGTTGTACCCTTACGGTTG 3',

R:
                                     (SEQ ID NO: 16)
5' TTTTGACTCTTGGGATCATTTATTC 3'
``` amplified a 251 nt region of the 008242F paralog in 20 Cannabis cultivars using PCR program 2. Thus, the c395 primer set amplifies both THCAS and CBDAS, while the c8242 primer set only amplifies CBDAS. We also used the previously-identified primer set (d589) that amplifies a 589 nt region within the archetypal THCA synthase gene (Staginnus et al., 2014), found in the PBBK assembly in scaffold 001774F (MXDB010001769.1) (SEQ ID NO:1). Using this primer set we amplified all 32 cultivars using program 1. These PCRs followed the standard protocol for Phusion® High-Fidelity PCR kit (New England Biosciences, Ipswich, Mass.), with the exception of using GC buffer instead of the standard HF buffer and the modified thermocycler programs in the following Table.

Thermocycler Programs Table: The thermocycler programs that we created for each of the primers we developed and used. Program 1 shows the program for both the c395, and d589 primer set PCRs. Program 2 describes the program we developed for the c8242 primer set PCR.

|  | Program 1 | Program 2 |
| --- | --- | --- |
| Initial Denaturation | 96° C. for 2 min | 98° C. for 3 min |
| Start Cycles: | 35 cycles | 30 cycles |
| Denaturation | 94° C. for 20 sec | 98° C. for 10 sec |
| Annealing | 62° C. for 30 sec | 63° C. for 30 sec |
| Elongation | 72° C. for 1 min 30 sec | 72° C. for 12 sec |
| Final Elongation | 72° C. for 5 min | 72° C. for 10 min |

The amplicons were trimmed in MEGA to remove low quality sequence ends so that each cultivar would have an equal sequence length. Due to low quality ends from Sanger Sequencing, the trimmed amplicons were 353 nt for samples amplified by primer set c395, 243 nt for samples amplified by primer set c8242, and 477 nt for samples amplified by primer set d589.

Neighbor-Joining (NJ) Tree Construction:

Since paralogs 000395F and 008242F are shown to be most related to the production of CBDA, we used the THCAS-like synthase (001769F) and the other known THCA synthases (Accession #: E33090) as outgroups when constructing the CBDA NJ trees. Conversely, because the c589 amplicon was shown to be most related to THCA production, we used the CBDA synthase paralogs 000395F, 000745F (MXDB010000745.1), and 008229F from the PBBK assembly and the other known CBDA synthase (Accession #: AB292682.1) as outgroups. The c395, c8242, and d589 amplicons were trimmed in MEGA to remove low quality sequence ends so that each cultivar would have an equal sequence length. Due to low quality ends from Sanger Sequencing, the trimmed amplicons were 353 nt for samples amplified by primer set c395; 243 nt for samples amplified by primer set c8242; and 477 nt for samples amplified by primer set d589. We constructed four NJ trees using CLC Sequence Viewer v. 8.0 (CITE). Each of these amplicons represents a different coding region of the synthase gene, each potentially distinct regarding selective pressures and thus yielding equally distinct monothetic phylogenies for a given cultivar or even paralog. We used blastn to identify berberine-bridge containing enzymes that were similar to cannabinoid synthases, which allowed us to compare all the cannabinoid-synthase-like genes in the PBBK assembly to the archetypal synthases to identify clades.

Genotype-Phenotype Correlation Using TASSEL:

A. Primer-Set-Specific Amplicons

We used TASSEL 5.0 (Bradbury, 2007) to seek correlations between the SNPs and the cannabinoid concentrations to understand whether SNPs found in these amplicons are correlated with cannabinoid content. We averaged the cannabinoid content by variety to compare genomic sequence to the phenotype. We corrected for relatedness between the varieties using the information from Lynch et al. 2016 for the c395, c8242, and d589 primers. This analysis was restricted to cultivars for which all three of the following were available: chemotypic data, relatedness, and Sanger-sequenced synthase amplicons. Consequently, there were 11 cultivars used for the c395 primer set, 13 cultivars for the c8242 primer set, 13 cultivars for the d589 primer set. When aligned to the published archetype THCAS gene (Genbank: E33090) (Masayama, 2000), high homology regions included bases 996-1345 for c395, bases 1238-1480 for c8242, and bases 288-764 for d589. We then performed a Mixed Linear Model (MLM) analysis using stringent TASSEL settings (re-estimate after each marker, and no compression) with a p-value filter of 1×10 3 to identify SNPs in the amplicons that are correlated to cannabinoid content.

B. Whole Genome Shotgun Analysis

To identify and investigate other polymorphic regions of the genome affecting cannabinoid bioaccumulation, we used the published distance matrix (Lynch et al., 2016), a published SNP table (Lynch et al., 2016) and the averaged chemotypes from Steep Hill (see Table of Cultivars selected for TASSEL Analysis), to perform a MLM analysis using TASSEL 5.0.

Table of Cultivars selected for TASSEL Analysis. Only samples that were included in Lynch et al.'s distance matrix, had chemotaxic data available, and that had successfully amplified were included in the downstream analysis. In total 30 different cultivars were included in this analysis, the c395 primer amplified 14 cultivars, c8242 amplified 18 cultivars, and d589 amplified 26 cultivars. The number 1 represents that that strain was included in the analysis for that primer; whereas, a 0 represents that the strain was not included in the analysis.

|  | c395 | c8242 | d589 |
|---|---|---|---|
| 707 Headband | 1 | 1 | 1 |
| ACDC | 1 | 1 | 1 |
| AK47 | 0 | 1 | 0 |
| Biodiesel | 0 | 0 | 1 |
| Blue Dream | 1 | 1 | 1 |
| C1 | 0 | 0 | 1 |
| C14 | 0 | 0 | 1 |
| C16 | 0 | 0 | 1 |
| C2 | 0 | 0 | 1 |
| C3 | 0 | 0 | 1 |
| C6 | 0 | 0 | 1 |
| Chem D | 1 | 1 | 1 |
| Chem D X Mass X NLS | 1 | 1 | 0 |
| Durban Poison | 1 | 1 | 1 |
| Girl Scout Cookies | 0 | 1 | 1 |
| Golden Goat | 1 | 1 | 1 |
| Gumbo | 0 | 1 | 1 |
| Harlequin | 1 | 1 | 1 |
| K19 | 0 | 0 | 1 |
| K2 | 0 | 0 | 1 |
| K3 | 0 | 0 | 1 |
| K9 | 0 | 0 | 1 |
| Kunduz | 1 | 1 | 1 |
| LA OG | 1 | 1 | 1 |
| OG18 | 1 | 1 | 1 |
| Otto #2 | 1 | 0 | 1 |
| Petrolia | 0 | 1 | 0 |
| Pre 93 Bubba Kush | 1 | 1 | 1 |
| Super Lemon Haze | 1 | 1 | 1 |
| White Widow | 0 | 1 | 0 |

The most significant SNPs were selected (36 SNPs, a s 1E-5 and effect size ≥23 or effect size ≤−23) and those scaffolds were analyzed for protein coding regions. Even though these SNPs were chosen due to their high significance, all SNPs found were significant since any confounding factors should have been eliminated with the genetic relatedness correction. Subsequently, we chose ORFs greater than 50 amino acids that were within 5,000 base pairs of the SNP to identify secondary marker proteins that were correlated to changes in cannabinoid content.

We identified thirteen SNPs that correlated with THCA levels and twenty-three SNPs that correlated with CDBA levels. Using BLAST's ORFFrinder Tool (Wheeler, 2003) and BLASTx (NCBI), we compared these ORFs to the most similar known proteins to find secondary marker proteins.

Example 1

Neighbor-Joining (NJ) Tree Construction

Figure 1B:
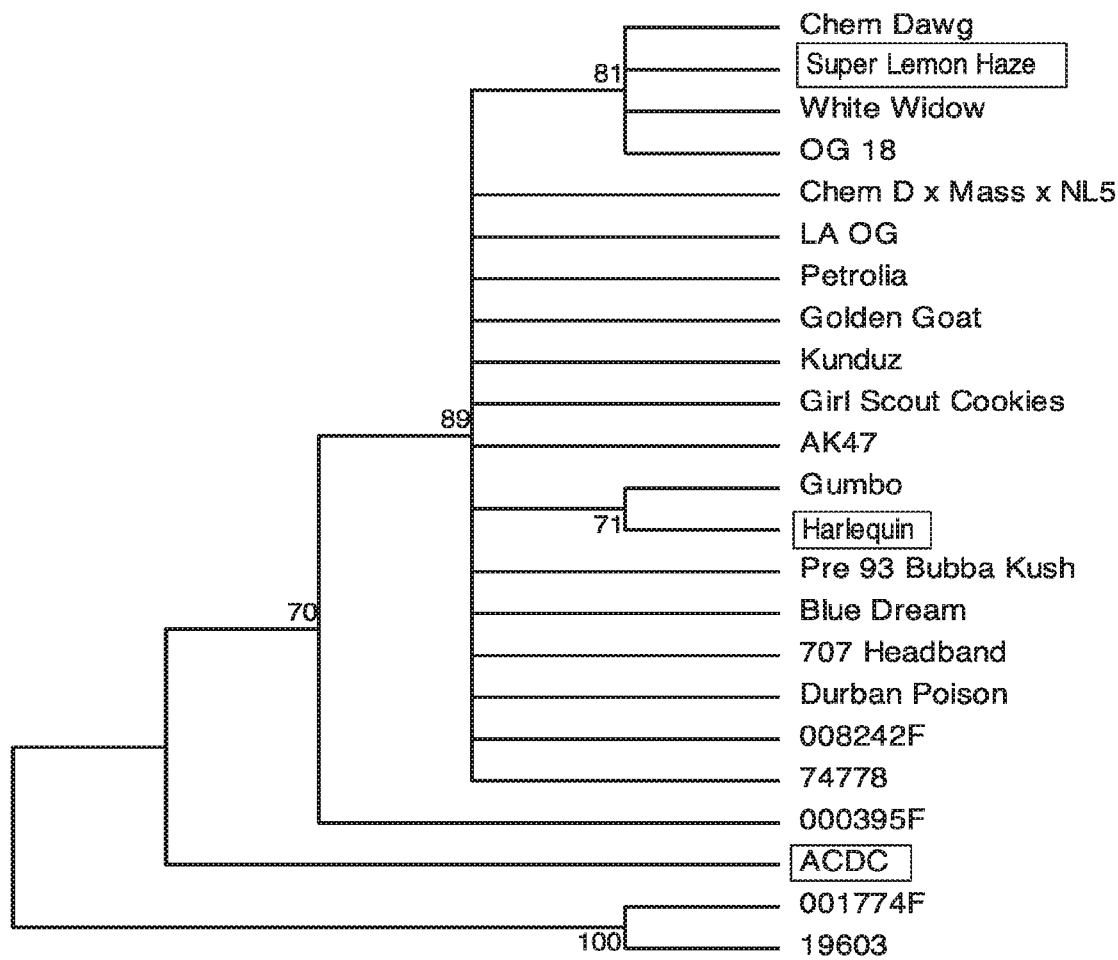
Figure 1C:
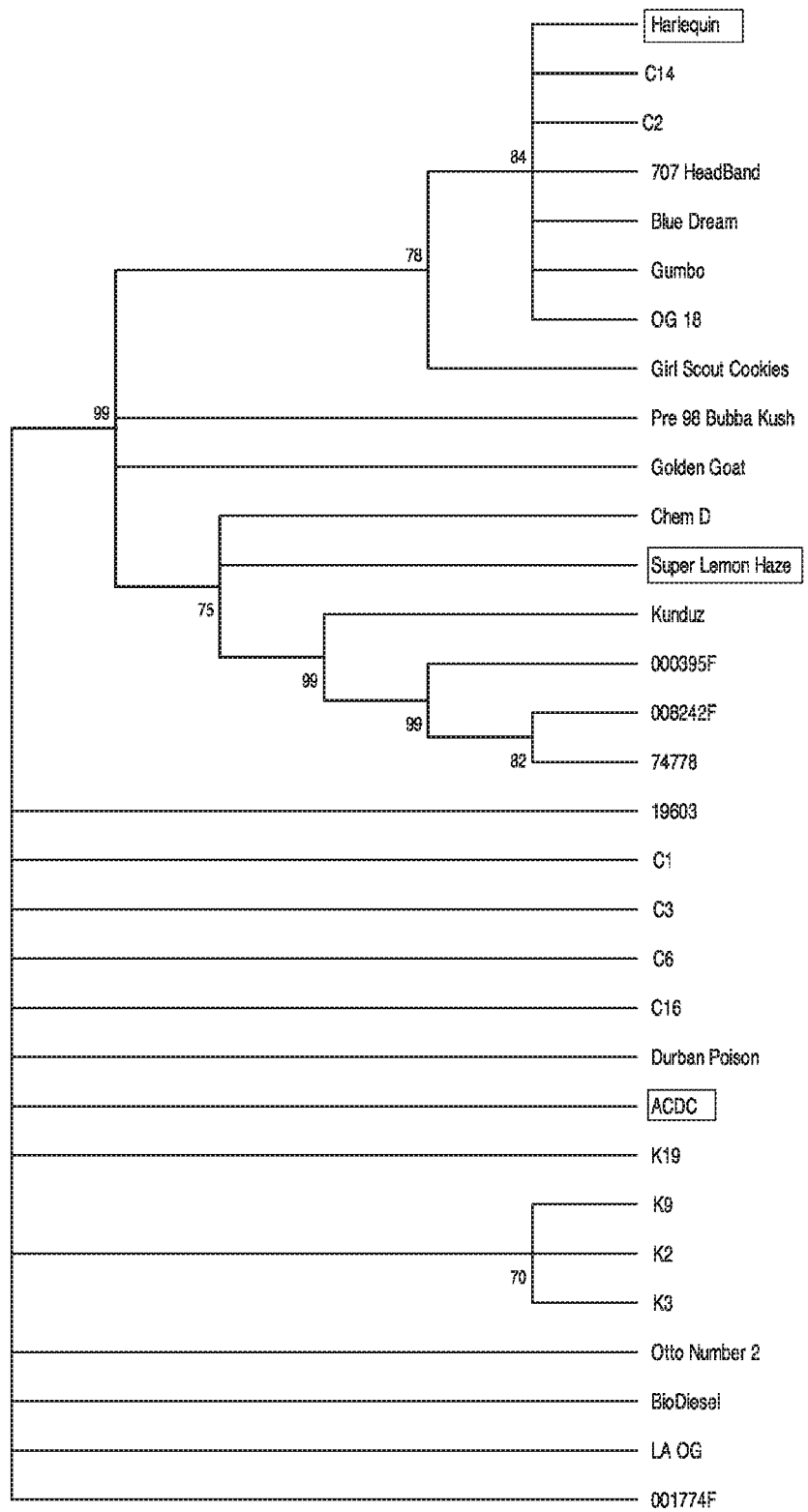
Figures 2A, 2B:
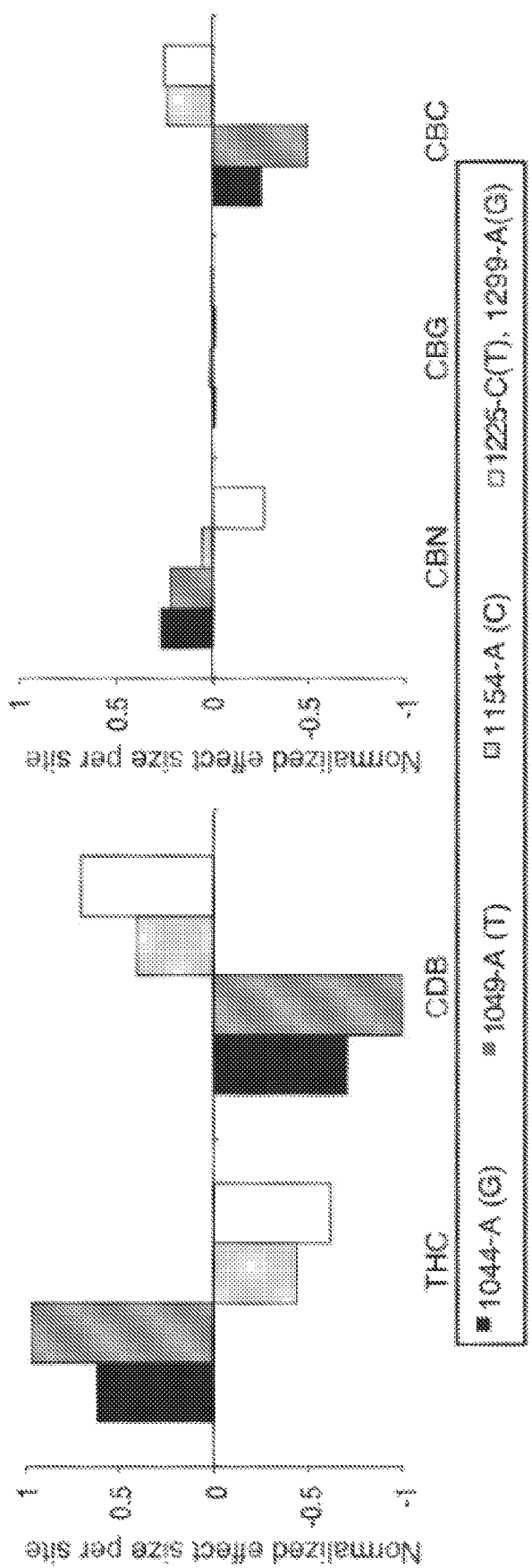
FIGS. 2A-2F show the Normalized Cannabinoid Effect Size for SNPs in three PCR amplicons. Each figure shows the normalized effect size in cannabinoid concentration of a given variety if it contains that SNP at a given position. Normalized effect size refers to the percent variation in cannabinoid content ranging between −1 to 1, to describe from −100%-100% change in percentage of that cannabinoid with that SNP present
Figures 2C, 2D:
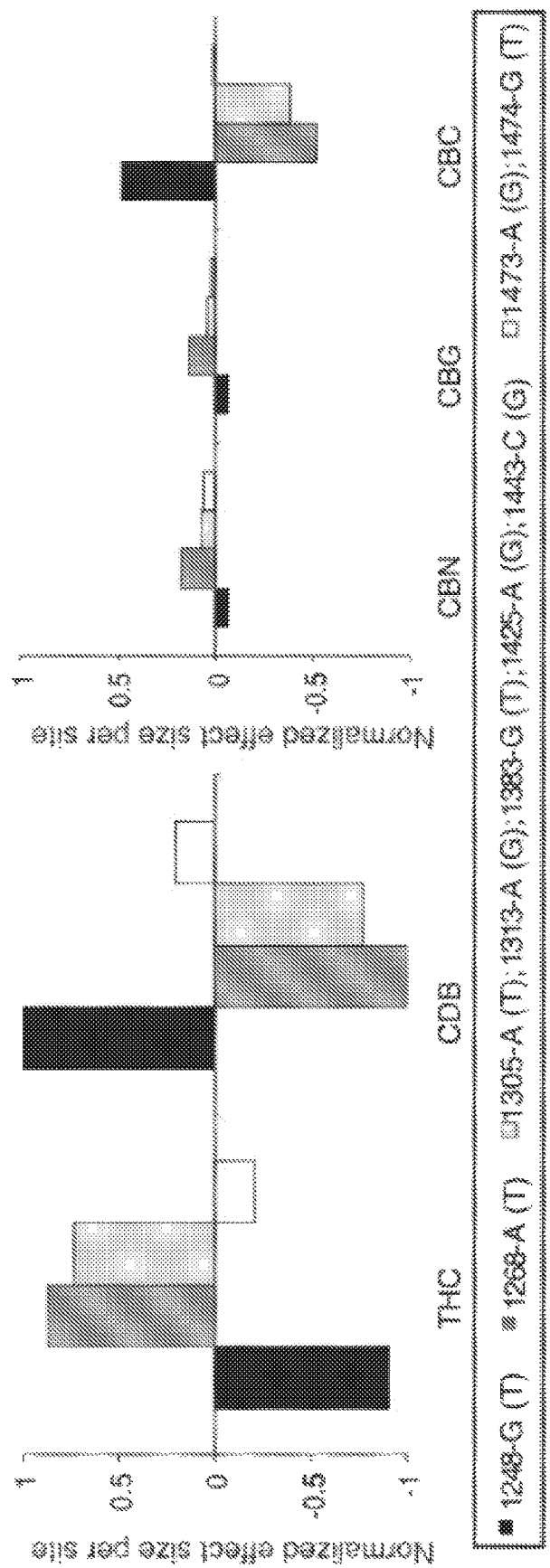
Figures 2E, 2F:
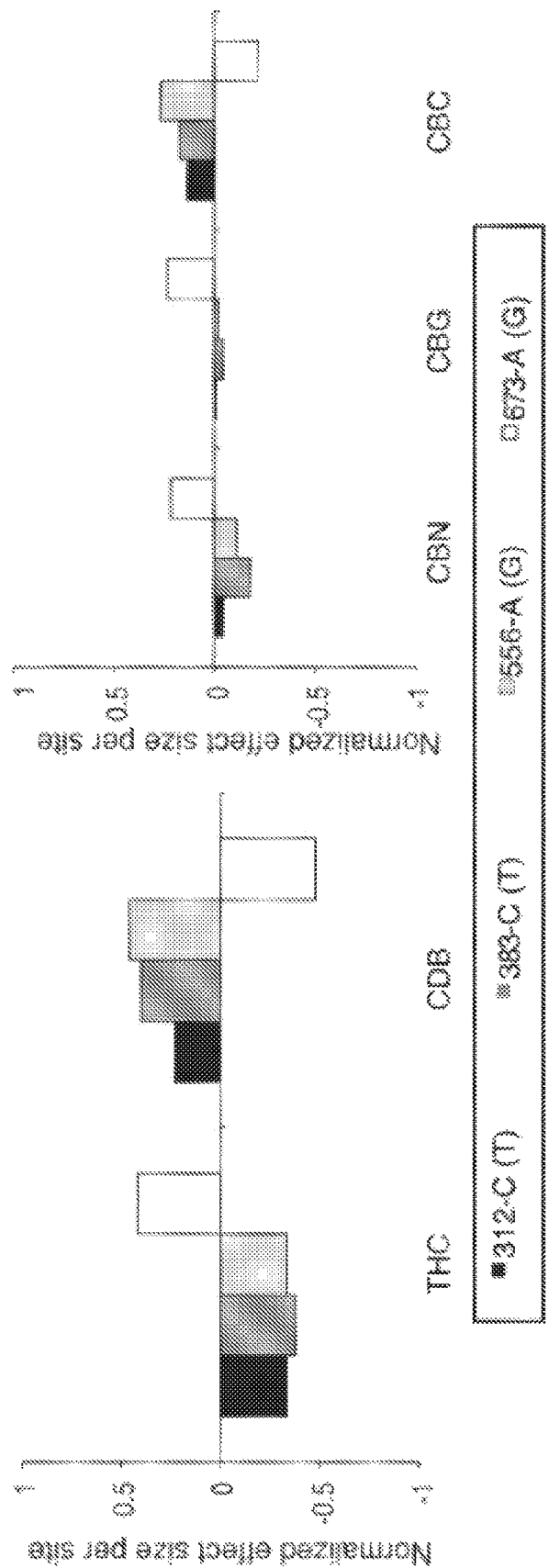

The NJ trees constructed from the amplicon sequences are markedly primer-set-dependent. The amplicons from the high CBDA producing cultivars such as Otto and Harlequin do not duster together using primer set c395 or c8242 (FIG. 1A). The amplicons from the four CBDA-related paralogs (000395F, 000745F, and 008242F from the PKB assembly, and AB292682.1) do not cluster together using primer set c395, but the 000745F and 008242F paralogs do group together with the c8242 primer set (FIGS. 1A and 1B). The amplicons from primer c8242 do not show any relationship between chemically similar cultivars (FIG. 1B). The tree constructed with the amplicons from primer c589 shows the clear phylogeny between cultivars since it dusters the known CBDAS together, although not all of the high CBD or high THC-producing cultivars cluster together (FIG. 1C). The final tree showed the phylogenetic relationship between all of the cannabinoid synthase-like genes identified in the PBBK assembly with the canonical THCA, CBDA, and CBCA synthases included for clade identification.

Example 2

Genotype-Phenotype Correlation Using TASSEL

A. Primer Amplicon Variation:

Using TASSEL's Mixed Linear Model (MLM) analysis, we identified 118 SNPs putatively related to cannabinoid ratios in the c395 amplicons, 57 in the c8242 amplicons, and 110 in the d589 amplicons.

Table of Chemical Profiles for Cultivars Used in Analyses: Average chemotypes of cultivars used for Tassel: These were the varieties that were included in the distance matrix and had been tested with our primers. The chemotype dataset was given by SteepHill Laboratories, which was filtered for the strains we used and then averaged based on strain name.

|  | THC % | CBD % | CBG % | CBN % | CBC % |
|---|---|---|---|---|---|
| Afghan Kush #1 | 18.076 | 0.033 | 1.967 | 0.000 | 0.000 |
| Afghan Kush #2 | 15.328 | 0.008 | 3.182 | 0.000 | 0.000 |
| Afghan Kush #3 | 7.343 | 0.000 | 0847 | 0.000 | 0.000 |
| Alaskan Thunderfuck | 6.706 | 0.045 | 0.484 | 0.012 | 0.084 |
| Blue Dream | 17.502 | 0.090 | 0.236 | 0.034 | 0.070 |
| Cannatonic | 4.397 | 11.063 | 0.466 | 0.021 | 0.140 |
| Carmagnola | 1.008 | 6.141 | 1.734 | 0.000 | 0.000 |
| Chocolope | 13.369 | 0.059 | 0.331 | 0.019 | 0.069 |
| Durban Poison | 16.226 | 0.066 | 0.694 | 0.018 | 0.048 |
| Girl Scout Cookies | 18.025 | 0.074 | 0.767 | 0.037 | 0.118 |
| Golden Goat | 14.862 | 0.023 | 0.474 | 0.013 | 0.002 |
| Grape Ape | 15.815 | 0.049 | 0.321 | 0.022 | 0.081 |
| Green Crack | 16.384 | 0.423 | 1.073 | 0.020 | 0.148 |
| Harlequin | 5.061 | 8.528 | 0.399 | 0.014 | 0.120 |
| Hindu Kush | 14.915 | 0.113 | 0.276 | 0.034 | 0.059 |
| Jack Herer | 16.680 | 0.447 | 0.897 | 0.017 | 0.037 |
| Kandy Kush | 16.028 | 0.060 | 0.427 | 0.015 | 0.072 |
| Maui Waui | 15.819 | 0.084 | 0.343 | 0.011 | 0.033 |
| OG Kush | 17.273 | 0.068 | 0.563 | 0.034 | 0.087 |
| Pre-98 Bubba Kush | 14.050 | 2.195 | 0.485 | 0.020 | 0.046 |
| Purple Kush | 16.069 | 0.070 | 0.399 | 0.021 | 0.081 |
| Super Lemon Haze | 15.325 | 0.061 | 1.005 | 0.049 | 0.064 |

Because the chemotaxic data contained other cannabinoids for some cultivars (as shown in the Table of Chemical Profiles for Cultivars Used in Analyses), we sorted the data to show the SNP sites that had the largest effect size correlated to THC and CBD concentration, because those cannabinoids were the focus of this study.

The effect size, shown in FIGS. 2A-2E, represents the variance in cannabinoid percentages between samples with distinct synthase-coding-sequence polymorphisms. The cultivars Durban Poison and Chemdawg contain polypeptide-truncating stop codons within the segment amplified with primer c395 (FIGS. 3A-3C), suggesting that the 0395.1 paralog was truncated in these cultivars.

B. Variation Throughout the Genome

Seeking other regions in the genome that may affect cannabinoid bioaccumulation, we used whole genome shotgun (WGS) data from 22 individuals to identify SNPs related to cannabinoid content using a MLM analysis method in TASSEL 5.0. We filtered the sites for a p-value ≥1E-5 and then sorted by the largest effect size. We kept sites with an effect size ≥23 or ≤-23 to identify the most significant sites out of the approximately 200.000 total SNPs analyzed. We then input the scaffolds of interest into BLAST's ORF finder to identify the closet 75+ amino acid ORF to the SNP called by Tassel, which is determined as the protein coding region of that SNP (as shown in the Table of Secondary Markers Associated with Cannabinoid Levels). There were eighteen hypothetical *Cannabis* proteins thus identified as associated THCA content, and five associated with CBDA content.

Table of Secondary Markers Associated with Cannabinoid Levels: BLAST Suite's ORF Finder identified the most similar known protein to each polypeptide sequence extracted from TASSEL. The scaffold name (second and third columns respectively refer to the number of the published PBBK genome scaffold bearing the SNP and sequence position. The fourth column lists the most relevant substitution allele at that locus. and the fifth the Effect Size score. Column six lists the closest protein homolog with the source-species given in brackets. Column seven lists the BLAST Accession number for the protein, and column eight, the gene position within the scaffold. A negative Effect score denotes a decrease in that cannabinoid --whereas, a positive Effect score denotes an increase-- associated with a given SNP.

| Trait | Scaffold | Site | Allele | Effect | Protein Observed | Accession | Region |
|---|---|---|---|---|---|---|---|
| Comb_CBD | 013042F | 6971 | A | 52 | No Protein around SNPs | | |
| | 001149F | 5367 | G | 61 | No Protein around SNPs | | |
| | 010624F | 14751 | A | 72 | No Protein around SNPs | | |
| | 009155F | 6762 | G | 133 | DNA/RNA polymerase superfamily protein [*Dorcoceras hygrometricum*] | KZV29964.1 | 13,954-14,484 |
| | 006754F | 30618 | A | 40 | No Protein around SNPs | | |
| | 005865F | 38199 | T | 25 | F-box/RNI-like/FBD-like domains-containing protein [*Arabidopsis thaliana*] | NP_199309.2 | 28,694-28,993 |
| | 003481F | 21372 | T | 24 | Small auxin-up RNA [*Parasponia andersonii*] | PON39100.2 | 24,532-25,131 |
| | 003481F | 21953 | C | 24 | Small auxin-up RNA [*Parasponia andersonii*] | PON39100.1 | 24,532-25,132 |
| | 003481F | 26146 | T | 24 | Small auxin-up RNA [*Parasponia andersonii*] | PON39100.0 | 24,532-25,133 |
| | 003481F | 26683 | C | 24 | Small auxin-up RNA [*Parasponia andersonii*] | PON39100.1 | 24,532-25,134 |
| | 000260F | 152661 | C | -334 | SAM-dependent methyltransferase [*Vibrio parahaemolytlcus*] | OOX29851.1 | 154,525-154,770 |
| | 011482F | 6838 | A | -308 | PREDICTED: *Juglans regia* protein MITOFERRINLIKE 1, chloroplastic (LOC109005387), mRNA | XM_018984311.1 | 9,081-9,598 |
| | 011482F | 6838 | G | -251 | PREDICTED: *Juglans regia* protein MITOFERRINLIKE 1, chloroplastic (LOC109005387), mRNA | XM_018984311.1 | 9,081-9,599 |

Table of Secondary Markers Associated with Cannabinoid Levels: BLAST Suite's ORF Finder identified the most similar known protein to each polypeptide sequence extracted from TASSEL. The scaffold name (second and third columns respectively refer to the number of the published PBBK genome scaffold bearing the SNP and sequence position. The fourth column lists the most relevant substitution allele at that locus, and the fifth the Effect Size score. Column six lists the closest protein homolog with the source-species given in brackets. Column seven lists the BLAST Accession number for the protein, and column eight, the gene position within the scaffold. A negative Effect score denotes a decrease in that cannabinoid --whereas, a positive Effect score denotes an increase-- associated with a given SNP.

| Trait | Scaffold | Site | Allele | Effect | Protein Observed | Accession | Region |
|---|---|---|---|---|---|---|---|
| Comb_THC | 001882F | 14364 | G | −25 | PREDICTED: *Ziziphus jujuba* pentatricopeptide repeat-containing protein At1g02150 (LOC107421758), mRNA | XM_016031081.1 | 22,856-23,443 |
| | 004056F | 980 | T | −25 | Chalcone and stilbene synthase family protein [*Arabidopsis thaliana*] | NP_196897.1 | 8,448-9,503 |
| | 001450F | 44588 | C | −25 | S-receptor-like serine/threonine-protein kinase [*Trema orientalis*] | PON79928.1 | 45,429-45,896 |
| | 001564F | 56899 | A | −24 | Powdery mildew resistance protein [*Parasponia andersonii*] | PON34600.1 | 63,899-64,618 |
| | 002204F | 17005 | A | −24 | PREDICTED: 5'-3' exoribonuclease 4-like isoform X2 [*Glycine max*] | XP_014629502.1 | 17,726-17,899 |
| | 002550F | 1400 | A | −24 | No Protein around SNPs | | |
| | 003602F | 2674 | C | −24 | No Protein around SNPs | | |
| | 000278F | 132696 | A | −24 | PREDICTED: ETHYLENE INSENSITIVE 3-like 1 protein [*Glycine max*] | XP_003519487.1 | 137,785-138,792 |
| | 001725F | 66867 | A | −24 | Retrovirus-related Pol polyprotein from transposon TNT 1-94 [*Glycine soja*] | KHN11334.1 | 66,945-67,151 |
| | 000707F | 70867 | C | −24 | PREDICTED: probable pectate lyase 8 [*Glycine max*] | XP_003555714.3 | 70,964-71,371 |
| | 000093F | 7083 | C | −24 | zinc knuckle (CCHC-type) family protein [*Arabidopsis thaliana*] | NP_189728.1 | 5,830-6,648 |
| | 002294F | 10311 | T | −24 | gag/pol protein [*Bryonia dioica*] | ADJ18449.1 | 11,716-11,880 |
| | 000730F | 80162 | C | −23 | hypothetical protein PanWU01x14_132560 [*Parasponia andersonii*] | PON63346.1 | 83940-84,329 |
| | 001554F | 10729 | A | −23 | Cyclin-dependent kinase inhibitor [*Trema orientalis*] | PON72921.1 | 7,611-8,216 |
| | 001554F | 10752 | A | −23 | Cyclin-dependent kinase inhibitor [*Trema orientalis*] | PON72921.2 | 7,611-8,217 |
| | 001554F | 10699 | T | −23 | Cyclin-dependent kinase inhibitor [*Trema orientalis*] | PON72921.3 | 7,611-8,218 |
| | 001814F | 2317 | C | −23 | Voltage dependent potassium channel [*Trema orientalis*] | POO03318.1 | 1,637-2,020 |
| | 001814F | 3188 | A | −23 | K-box region protein (DUF1985) [*Arabidopsis thaliana*] | NP_001321227.1 | 161,149-161,913 |
| | 000253F | 88574 | G | −23 | MYB transcription factor [*Trema orientalis*] | PON92936.1 | 83,629-84,291 |
| | 002976F | 37970 | G | −23 | ty3-gypsy retrotransposon protein [*Cucumis melo* subsp. *melo*] | ADN34002.1 | 33,914-34,258 |
| | 000209F | 125278 | G | 48 | Glycosyl transferase [*Parasponia andersonii*] | PON50067.1 | 124,028-124,366 |
| | 000209F | 125278 | A | 27 | Glycosyl transferase [*Parasponia andersonii*] | PON50067.1 | 124,028-124,366 |
| | 000807F | 64363 | A | 24 | retrotransposon protein, putative, Ty1-copia subclass [*Oryza sativa* Japonica Group] | ABA98656.1 | 64,022-65,611 |

Example 3

Morphological Changes in Folded Enzymes

Through modeling the enzymes on I-Tasser, we concluded that there were structural and enzymatic differences between different cultivars and paralogs. The cultivars were classified into three groups that were representative of each phylogenetic cluster of the ML trees. A representative strain was chosen from each: Super Lemon Haze, Harlequin, and ACDC. Using the complete 1635 bp THCA synthase gene to model the enzyme folding, we found the amino acid sequence similarity to THCA synthase ranged from 78% to 97.4% similar (see Table of I-Tasser Structure Prediction Analysis). Furthermore, this analysis showed that the binding affinity for FAD, a cofactor in the conversion of CBGA to THCA, differed between the hypothetical synthases. We observed the lowest binding affinity (with a C-Score of 0.83) for the SLH strain in the 0008242F paralog, as well as the highest affinity (with a C-Score of 0.9) in the SLH and ACDC strains in the 0001774F paralog (SEQ ID NO:1). These binding affinities were calculated using automatically generated binding sites based on the folded enzyme conformation. The amino acid sites I-Tasser identified as interacting with FAD were amino acid residues 69, 109, 110, 111, 112, 113, 114, 115, 116, 119, 120, 132, 151, 174, 175, 176, 179, 180, 182, 183, 184, 186, 189, 190, 235, 239, 240, 241, 481, 483, and 533.

Table of I-Tasser Structure Prediction Analysis. I-Tasser Structure Prediction Tools were used to model the structural changes to the synthase enzyme due to the variance we observed in the amplified region. The Identity is the percentage sequence identity in the structurally aligned region to the known THCA Synthase Enzyme (PDB:3vteA). The TM-Score describes the rating between the query structure and known structures in the PDB library. The root-mean-standard-deviation (RMSD) describes the variance between residues that are structurally aligned by TM-align. Coverage represents the coverage of the alignment by TM-align and is equal to the number of structurally aligned residues divided by length of the query protein. The confidence score (C-Score) ranges [0-1], where a higher score indicates a more reliable prediction to binding to the FAD (PDB:3w8wA) ligand determined by the COACH program.

|  | c395 | | | d589 | | | c8242 | | |
| --- | --- | --- | --- | --- | --- | --- | --- | --- | --- |
| STRAIN: | SLH | ACDC | HQ | SLH | ACDC | HQ | SLH | ACDC | HQ |
| Identity | 0.838 | 0.834 | 0.828 | 0.936 | 0.974 | 0.956 | 0.78 | 0.834 | 0.817 |
| TM-Score | 0.919 | 0.917 | 0.919 | 0.918 | 0.918 | 0.886 | 0.898 | 0.917 | 0.915 |
| RMSD | 0.42 | 0.5 | 0.41 | 0.37 | 0.49 | 0.37 | 1.39 | 0.54 | 0.65 |
| Coverage | 0.921 | 0.921 | 0.921 | 0.92 | 0.921 | 0.921 | 0.919 | 0.921 | 0.92 |
| Cscore - 3w8wA | 0.88 | 0.86 | 0.84 | 0.9 | 0.9 | 0.87 | 0.83 | 0.86 | 0.88 |

DISCUSSION

In the past few years, the understanding of cannabinoid synthases has greatly advanced, which portrays a more complex system than previously thought. These enzymes were originally described as a single locus with two codominant alleles (de Meijer et al., 2003), although multiple pseudogenes and paralogs of these synthases in the genome were recently discovered (McKernan et al. 2015). Recent research established that the genes related to CBDAS and THCAS were in very close proximity, and that multiple loci might be related to the production and expression of both compounds (Weiblein et al. 2015). Our studies agree that multiple loci are involved in cannabinoid production, through the identification and targeting of these synthase genes in numerous cultivars.

While primer sets have been developed for the single loci allele model of THCAS gene, these fail to test for the newly discovered paralogs, which have been shown to correlate to cannabinoid content. The primers c395 and c8242 of this disclosure are specific to the paralogs on the 0395.1 and 8242.1 scaffolds of the PBBK assembly, however, the c395 reverse primer has two binding sites in the genome, which leads to lower quality sanger sequencing than the c8242 primer set.

Through testing multiple areas within the synthase paralogs, we discovered the primers' amplicons show different degrees of variation between cultivars. This suggests that some primer sets, and therefore paralogs, were better indicators of phylogeny. However, when comparing monothetic trees based on internal segments of the synthase to the previously-published phylogenetic relationship between Cannabis varieties (Lynch et al. 2016) constructed from full-length alignments using GBS and WGS data, we find the former are less informative and less consistent. Both the c395 and d589 primers resolve some of the high-THCA and high-CBDA varieties into groups; however, their respective monothetic phylogenies fail to distinguish all cultivars correctly (FIGS. 1A and 1C).

The d589 tree (FIG. 1C), shows the best segregation of cultivars for cannabinoid content and groups the known synthases together, which suggests this region of the synthase is likely responsible for product specificity. The c8242 primer set is the least phylogenetically descriptive primers since most cultivars similar in chemotypes are not in the same clades, which suggests that the regions amplified from these primers are highly conserved among the varieties with very few informative polymorphisms.

While the synthase enzymes are a necessary component of cannabinoid bioaccumulation, other regions of the genome also potentially contribute, especially those encoding enzymes responsible for upstream precursors such as olivetolic acid (Taura, 2009). Weiblen et al. (2015) suggested the trichome genes as an area of interest. Although genes controlling upstream biosynthesis and trichome development lacked correlation to cannabinoid content in the TASSEL analysis of the WGS reads, it appears that hormonal-response-factor-like proteins, kinase-like proteins, and DNA/RNA-binding-like proteins potentially have key roles in chemotype development. In Arabidopsis thaliana, a group of hormone-responsive transcription factors—the ethylene-responsive-element-binding factors (ERF)—control the production of secondary metabolites against pathogens (Singh et al., 2002), providing both a precedent and model for our above-cited findings.

While this research is a significant improvement in our grasp of the cannabinoid biosynthetic pathway, there is still much to be learned about this complex system of enzymes. The paralog identification markers we developed can be used by breeders to control the presence or absence of certain synthase activities within their cultivars and increase the speed of selective breeding dramatically. Furthermore, these markers can be implemented in various high-throughput screening protocols such as qPCR, HRM, DGGE, and other amplicon-based screening methodologies. Additionally, this new marker system can be used by governmental agencies to identify drug-producing cultivars, where the possession of such plants is still illegal.

REFERENCES van Bakel, H., Stout, J. M., Cote, A. G., Tallon, C. M., Sharpe, A. G., Hughes, T. R., and Page, J. E. (2011). The draft genome and transcriptome of Cannabis sativa. Genome Biology 12, R102.

Bell, C. D., Soltis, D. E., and Soltis, P. S. (2010). The age and diversification of the angiosperms re-revisited. American Journal of Botany 97, 1296-1303.

Bradbury, P. J., Zhang, Z., Kroon, D. E., Casstevens, T. M., Ramdoss, Y., and Buckler, E. S. (2007). TASSEL: software for association mapping of complex traits in diverse samples. Bioinformatics 23, 2633-2635.

Cheng, P., Holdsworth, W., Ma, Y., Coyne, C. J., Mazourek, M., Grusak, M. A., Fuchs, S., and McGee, R. J. (2015). Association mapping of agronomic and quality traits in USDA pea single-plant collection. Molecular Breeding 35.

Delledonne, M., Xia, Y., Dixon, R. A., and Lamb, C. (1998). Nitric oxide functions as a signal in plant disease resistance. Nature 394, 585-588.

ElSohly, M. A., and Slade, D. (2005). Chemical constituents of marijuana: The complex mixture of natural cannabinoids. Life Sciences 78, 539-548.

Gagne, S. J., Stout, J. M., Liu, E., Boubakir, Z., Clark, S. M., and Page, J. E. (2012). Identification of olivetolic acid cydase from Cannabis sativa reveals a unique catalytic route to plant polyketides. Proceedings of the National Academy of Sciences 109, 12811-12816.

Gaines, T. A., Zhang, W., Wang, D., Bukun, B., Chisholm, S. T., Shaner, D. L., Nissen, S. J., Patzoldt, W. L., Tranel, P. J., Culpepper, A. S., et al. (2010). Gene amplification confers glyphosate resistance in Amaranthus palmeri Proceedings of the National Academy of Sciences 107, 1029-1034.

Kumar, S., Stecher, G., and Tamura, K. (2016). MEGA7: Molecular Evolutionary Genetics Analysis Version 7.0 for Bigger Datasets. Molecular Biology and Evolution 33, 1870-1874.

Langenheim, J. H. (1994). Higher plant terpenoids: A phytocentric overview of their ecological roles. Journal of Chemical Ecology 20, 1223-1280.

McPartland, J. M., Clarke, R. C., and Watson, D. P. (2000). Hemp diseases and pests: management and biological control: an advanced treatise (New York, N.Y.: CABI Pub).

de Meijer, E. P. M., Bagatta, M., Carboni, A., Crucitti, P., Molitemi, V. M. C., Ranalli, P., and Mandolino, G. (2003). The inheritance of chemical phenotype in Cannabis sativa L. Genetics 163, 335-348.

Makemon, 2015

Mills, G. C., Alperin, J. B., and Trimmer, K. B. (1975). Studies on variant glucose-6-phosphate dehydrogenases: G6PD Fort Worth. Biochem Med 13, 264-275.

Onofri, C., de Meijer, E. P. M., and Mandolino, G. (2015). Sequence heterogeneity of cannabidiolic- and tetrahydrocannabinolic acid-synthase in Cannabis sativa L. and its relationship with chemical phenotype. Phytochemistry 116, 57-68.

Page, J. C. Aromatic prenyltransferase from Cannabis.

Radwan, M. M., ElSohly, M. A., EI-Alfy, A. T., Ahmed, S. A., Slade, D., Husni, A. S., Manly, S. P., Wilson, L., Seale, S., Cutler, S. J., et al. (2015). Isolation and Pharmacological Evaluation of Minor Cannabinoids from High-Potency Cannabis sativa. Journal of Natural Products 78, 1271-1276.

Ravikumar, C., Veerendrakumar, M., Hegde, T., Nagaraja, D., Jayakumar, P. N., and Shankar, S. K. (1996). Basal ganglionic angioleiomyoma. Clin Neurol Neurosurg 98, 253-257.

Roy, A., Kucukural, A., and Zhang, Y. (2010). I-TASSER: a unified platform for automated protein structure and function prediction. Nature Protocols 5, 725-738.

Russo, E. B. (2011). Taming THC: potential cannabis synergy and phytocannabinoid-terpenoid entourage effects: Phytocannabinoid-terpenoid entourage effects. British Journal of Pharmacology 163, 1344-1364.

Russo, E. B., and McPartland, J. M. (2003). Cannabis is more than simply A9-tetrahydrocannabinol. Psychopharmacology 165, 431-432.

Shoyama, Y., Yagi, M., Nishioka, I., and Yamauchi, T. (1975). Biosynthesis of cannabinoid acids. Phytochemistry 14, 2189-2192.

Shoyama, Y., Tamada, T., Kurihara, K., Takeuchi, A., Taura, F., Arai, S., Blaber, M., Shoyama, Y., Morimoto. S., and Kuroki. R. (2012). Structure and Function of Δ1-Tetrahydrocannabinolic Acid (THCA) Synthase, the Enzyme Controlling the Psychoactivity of Cannabis sativa. Journal of Molecular Biology 423, 96-105.

Singh, K. (2002). Transcription factors in plant defense and stress responses. Current Opinion in Plant Biology 5, 430-436.

Sirikantaramas, S. (2005). Tetrahydrocannabinolic Acid Synthase, the Enzyme Controlling Marijuana Psychoactivity, is Secreted into the Storage Cavity of the Glandular Trichomes. Plant and Cell Physiology 46, 1578-1582.

Soltis, D. E., Soltis, P. S., and Chase, M. W. (2006). Phylogeny and Evolution of Angiosperms. International Journal of Plant Sciences 167, 607-611.

Staginnus, C., ZOmtlein, S., and de Meijer, E. (2014). A PCR marker Linked to a THCA synthase Polymorphism is a Reliable Tool to Discriminate Potentially THC-Rich Plants of Cannabis sativa L. Journal of Forensic Sciences 59, 919-926.

Swift, W., Wong, A., Li, K. M., Arnold, J. C., and McGregor, I. S. (2013). Analysis of Cannabis Seizures in NSW, Australia: Cannabis Potency and Cannabinoid Profile. PLoS ONE 8, e70052.

Untergasser, A., Cutcutache, I., Koressaar, T., Ye, J., Faircloth, B. C., Remm, M., and Rozen, S. G. (2012). Primer3-new capabilities and interfaces. Nucleic Acids Research 40, e11-e115.

Vergara, D., Baker, H., Clancy, K., Keepers, K. G., Mendieta, J. P., Pauli, C. S., Tittes, S. B., White, K. H., and Kane, N. C. (2016). Genetic and Genomic Tools for Cannabis sativa. Critical Reviews in Plant Sciences 35, 364-377.

Weiblen, G. D., Wenger, J. P., Craft, K. J., ElSohly, M. A., Mehmedic, Z., Treiber, E. L., and Marks, M. D. (2015). Gene duplication and divergence affecting drug content in Cannabis sativa. New Phytologist 208, 1241-1250.

Wheeler, D. L., Church, D. M., Federhen, S., Lash, A. E., Madden, T. L., Pontius, J. U., Schuler, G. D., Schriml, L. M., Sequeira, E., Tatusova, T. A., et al. (2003). Database resources of the National Center for Biotechnology. Nudeic Acids Res. 31, 28-33.

Yang, J., Yan, R., Roy, A., Xu, D., Poisson, J., and Zhang, Y. (2015). The I-TASSER Suite: protein structure and function prediction. Nat. Methods 12, 7-8.

Yu, J., and Buckler, E. S. (2006). Genetic association mapping and genome organization of maize. Current Opinion in Biotechnology 17, 155-160.

Żmieńko, A., Samelak, A., Kozlowski, P., and Figlerowicz, M. (2014). Copy number polymorphism in plant genomes. Theoretical and Applied Genetics 127, 1-18.

Zhu, C., Gore, M., Buckler, E. S., and Yu, J. (2008). Status and Prospects of Association Mapping in Plants. The Plant Genome Journal 1, 5.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A method for producing a cannabis plant cultivar, comprising:

identifying one or more single-locus non-functional paralogs of a cannabinoid synthase gene in two or more cannabis plant cultivars wherein the identified non-functional paralogs correspond to either a functional paralog or a non-functional paralog of the cannabinoid synthase gene, and the identifying comprises PCR amplification using a primer set selected from the group consisting of:

a) the primer set:
F:
(SEQ ID NO: 13)
5' TCACCTCTAACACAACCCCAAAA 3'

R:
(SEQ ID NO: 14)
5' CCAAAAGAGA TCTTCCCCCA TA 3'
and b) the primer set:
F:
(SEQ ID NO: 15)
5' GCGTTGTACCCTTACGGTTG 3'

R:
(SEQ ID NO: 16)
5' TTTTGACTCTTGGGATCATTTATTC 3' and
crossbreeding two individual cannabis plant cultivars identified to have desired effects on cannabinoid production in the cannabis plant.

2. The method of claim 1, wherein the cannabinoid synthase gene is selected from delta-9-tetrahydrocannabinolic acid (THCA) and Cannabidolic acid (CBDA) synthase.

3. The method of claim 1, wherein the cannabinoid synthase gene is CBDA synthase.

4. The method. of claim 1, wherein the identifying comprises PCR amplification of a composition comprising genomic DNA or cDNA from the two or more cannabis plant cultivars.

5. The method of claim 1, wherein the crossbreeding selects for a cannabis plant cultivar having a greater CBDA content than the two identified individual cannabis plant cultivars.

6. The method of claim 1. wherein the crossbreeding selects for a cannabis plant cultivar having a lower CBDA content than the two identified individual cannabis plant cultivars.

7. The method of claim 5, wherein the CBDA content of the cannabis plant cultivar resulting from the crossbreeding step is a result of i) greater enzymatic activity of a functional CBDA synthase paralog identified in two or more cannabis plant, cultivars; or ii) greater copy number of a functional CBDA synthase paralog.

8. The method of claim 1, wherein the identified non-functional paralog comprises at least one of paralogs 008242 and 00395, wherein 008242 and 00395 comprise CBDA synthase paralogs and are located on a scaffold 08242F having scaffold accession number MXDB010008229.1 and. 00395F having scaffold accession number MXDB01000395.1 respectively of a Pineapple-Banana-Bubba-Kush (PBBK) marijuana cultivar.

9. The method of claim 1, wherein said crossbreeding further comprises crossing a first cannabis plant, wherein said first cannabis plant provides desired. cannabinoid. content using the identified non-functional. paralogs with a second cannabis plant having a desired effect on cannabinoid production, and harvesting the resultant hybrid cannabis seed.

10. The method of claim 1., wherein said crossbreeding further comprises introgressing CBDA production into hybrid cannabis seed.

11. The method of claim 1., wherein said crossbreeding further comprises one or more of a backcrossing, an outcrossing, and a self-crossing.

12. A method for producing a cannabis plant cultivar, comprising:
   identifying one or more single-locus non-functional paralogs of a cannabinoid synthase gene in two or more cannabis plant cultivars wherein the identified non-functional paralogs correspond to either a functional paralog or a non-functional paralog of the cannabinoid synthase gene; and
   crossbreeding two individual cannabis plant cultivars identified to have desired effects on cannabinoid production in the cannabis plant, wherein the cannabis cultivar comprises one or more DNA molecular markers associated with. CBDA synthase activity, the one or more DNA molecular markers comprising a nucleotide sequence that encodes an amino acid substitution identified in any one of the CBDA synthase amino acid. substitutions of FIGS. 3A-3C.

13. The method of claim 12, wherein said identifying paralogs of a cannabinoid synthase gene further comprises molecular marker analysis of DNA samples isolated from one or more of a progeny plant, a second cannabis plant, a high CBDA producing cannabis cultivar, a parental cannabis cultivar, and a low CBDA producing cannabis cultivar, wherein said analysis identifies DNA molecules associated. with CBDA. content in the cannabis plant.

14. The method of claim 13, wherein the molecular marker is a single nucleotide polymorphism (SNP).

15. The method of claim 5, wherein the CBDA content of the cannabis plant cultivar resulting from the crossbreeding step is a result of i) greater enzymatic activity of a CBDA paralog identified in two or more cannabis plant cultivars; or ii) greater copy number of a CBDA.

16. The method of claim 5, wherein the CBDA content of the cannabis plant cultivar resulting from the crossbreeding step i.s a result of i) lesser enzymatic activity of a non-functional THCA synthase paralog identified in two or more cannabis plant cultivars; or ii) lesser copy number of a non-functional THCA synthase paralog.

17. The method of claim 6, wherein the CBDA content of the cannabis plant cultivar resulting from the crossbreeding step is a result of i) greater enzymatic activity of a functional THCA synthase paralog identified in two or more cannabis plant cultivars; or if) greater copy number of a functional THCA synthase paralog.

18. The method of claim 6, wherein the CBDA content of the cannabis plant cultivar resulting from the crossbreeding step is a result of i.) lesser enzymatic activity of a non-functional CBDA syntha.se paralog identified in two or more cannabis plant cultivars; or ii) lesser copy number of a non-functional CBDA. synthase paralog.

19. The method of claim 12, wherein the identifying comprises PCR amplification of the one or more DNA molecular markers using a primer set selected from the group consisting of:

```
                                     (SEQ ID NO: 13)
5' TCACCTCTAACACAACCCCAAAA 3'

(SEQ ID NO: 14)
5' CCAAAAGAGATCTTCCCCCATA 3'

(SEQ ID NO: 15)
5' GCGTTGTACCCCTTACGGTTG 3',
and (SEQ ID NO: 16)
5' TTTTGACTCTTGGGATCATTTATTC 3'
```

* * * * *

SEQUENCE LISTING

<160> NUMBER OF SEQ ID NOS: 16

<210> SEQ ID NO 1
<211> LENGTH: 1638
<212> TYPE: DNA
<213> ORGANISM: Cannabis sativa

<400> SEQUENCE: 1

```
atgaattgct cagcattttc cttttggttt gtttgcaaaa taatatttttt ctttctctca      60 ttccatatcc aaatttcaat agctaatcct cgagaaaact tccttaaatg cttctcaaaa     120
catattccca acaatgtagc aaatccaaaa ctcgtataca ctcaacacga ccaattgtat     180
atgtctatcc tgaattcgac aatacaaaat cttagattca tctctgatac aaccccaaaa     240
ccactcgtta ttgtcactcc ttcaaataac tcccatatcc aagcaactat tttatgctct     300
aagaaagttg gcttgcagat tcgaactcga agcggtggcc atgatgctga gggtatgtcc     360
tacatatctc aagtcccatt tgttgtagta gacttgagaa acatgcattc gatcaaaata     420
gatgttcata gccaaactgc gtgggttgaa gccggagcta cccttggaga agtttattat     480
tggatcaatg agaagaatga gaatcttagt tttcctggtg ggtattgccc tactgttggc     540
gtaggtggac actttagtgg aggaggctat ggagcattga tgcgaaatta tggccttgcg     600
gctgataata ttattgatgc acacttagtc aatgttgatg aaaagttct agatcgaaaa     660 tccatgggag aagatctgtt ttgggctata cgtggtggtg gaggagaaaa ctttggaatc     720
attgcagcat ggaaaatcaa actggttgct gtcccatcaa agtctactat attcagtgtt     780
aaaaagaaca tggagataca tgggcttgtc aagttattta acaaatggca aaatattgct     840
tacaagtatg acaaagattt agtactcatg actcacttca taacaaagaa tattacagat     900
aatcatggga agaataagac tacagtacat ggttacttct cttcaatttt tcatggtgga     960
gtggatagtc tagtcgactt gatgaacaag agctttcctg agttgggtat taaaaaaact    1020
gattgcaaag aatttagctg gattgataca accatcttct acagtggtgt tgtaaatttt    1080
aacactgcta atttttaaaaa ggaaattttg cttgatagat cagctgggaa gaagacggct    1140
ttctcaatta agttagacta tgttaagaaa ccaattccag aaactgcaat ggtcaaaatt    1200
```

-continued

```
ttggaaaaat tatatgaaga agatgtagga gctgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgtttataa ttttacgact cctatgtgt cccaaaatcc aagattggcg     1440
tatctcaatt atagggacct tgatttagga aaaactaatc atgcgagtcc taataattac    1500
acacaagcac gtatttgggg tgaaaagtat tttggtaaaa attttaacag gttagttaag    1560
gtgaaaacta agttgatcc caataatttt tttagaaacg aacaaagtat cccacctctt     1620
ccaccgcatc atcattaa                                                  1638
```

<210> SEQ ID NO 2
<211> LENGTH: 545
<212> TYPE: PRT
<213> ORGANISM: Cannabis sativa

<400> SEQUENCE: 2

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Glu Asn Phe Gly Ile
225                 230                 235                 240

Ile Ala Ala Trp Lys Ile Lys Leu Val Ala Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
```

```
                290                 295                 300
Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
                340                 345                 350

Phe Tyr Ser Gly Val Val Asn Phe Asn Thr Ala Asn Phe Lys Lys Glu
                355                 360                 365

Ile Leu Leu Asp Arg Ser Ala Gly Lys Lys Thr Ala Phe Ser Ile Lys
                370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
                405                 410                 415

Tyr Pro Tyr Gly Gly Ile Met Glu Glu Ile Ser Glu Ser Ala Ile Pro
                420                 425                 430

Phe Pro His Arg Ala Gly Ile Met Tyr Glu Leu Trp Tyr Thr Ala Ser
                435                 440                 445

Trp Glu Lys Gln Glu Asp Asn Glu Lys His Ile Asn Trp Val Arg Ser
                450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
                485                 490                 495

Pro Asn Asn Tyr Thr Gln Ala Arg Ile Trp Gly Glu Lys Tyr Phe Gly
                500                 505                 510

Lys Asn Phe Asn Arg Leu Val Lys Val Lys Thr Lys Val Asp Pro Asn
                515                 520                 525

Asn Phe Phe Arg Asn Glu Gln Ser Ile Pro Pro Leu Pro Pro His His
                530                 535                 540

His
545

<210> SEQ ID NO 3
<211> LENGTH: 1638
<212> TYPE: DNA
<213> ORGANISM: Cannabis sativa

<400> SEQUENCE: 3
atgaattgct caacattctc cttttggttt gtttgcaaaa taatattttt ctttctctca      60
ttcaatatcc aaatttcaat agctaatcct caagaaaact tccttaaatg cttctcggaa     120
tatattccta caatccagc aaatccaaaa ttcatataca ctcaacacga ccaattgtat      180
atgtctgtcc tgaattcgac aatacaaaat cttagattca cctctgatac aaccccaaaa     240
ccactcgtta ttgtcactcc ttcaaatgtc tcccatatcc aggccagtat tctctgctcc     300
aagaaagttg gtttgcagat tcgaactcga agcggtggcc atgatgctga gggtttgtcc     360
tacatatctc aagtcccatt tgctatagta gacttgagaa acatgcatac ggtcaaagta     420
gatattcata gccaaactgc gtgggttgaa gccggagcta cccttggaga gtttattat      480 tggatcaatg agatgaatga gaatttagt tttcctggtg ggtattgccc tactgttggc      540
gtaggtggac actttagtgg aggaggctat ggagcattga tgcgaaatta tggccttgcg     600
gctgataata tcattgatgc acacttagtc aatgttgatg aaaagttct agatcgaaaa     660
```

-continued

```
tccatgggag aagatctatt ttgggctata cgtggtggag gaggagaaaa ctttgtaatc    720
attgcagcat ggaaaatcaa acttgttgtt gtcccatcaa aggctactat attcagtgtt    780
aaaaagaaca tggagataca tggcttgtc aagttattta acaaatggca aaatattgct    840
tacaagtatg acaaagattt aatgctcacg actcacttca gaactaggaa tattacagat    900
aatcatggga agaataagac tacagtacat ggttacttct cttccatttt tcttggtgga    960
gtggatagtc tagttgactt gatgaacaag agctttcctg agttgggtat taaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta agttagacta tgttaagaaa ctaatacctg aaactgcaat ggtcaaaatt   1200
ttggaaaaat tatatgaaga agaggtagga gttgggatgt atgtgttgta cccttacggt   1260
ggtataatgg atgagatttc agaatcagca attccattcc ctcatcgagc tggaataatg   1320
tatgaacttt ggtacactgc tacctgggag aagcaagaag ataacgaaaa gcatataaac   1380
tgggttcgaa gtgtttataa tttcacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca aagctgatcc caataatttt tttagaaacg aacaaagtat cccacctctt   1620
ccaccgcgtc atcattaa                                                  1638
```

```

<210> SEQ ID NO 4
<211> LENGTH: 545
<212> TYPE: PRT
<213> ORGANISM: Cannabis sativa

<400> SEQUENCE: 4

Met Asn Cys Ser Thr Phe Ser Phe Trp Phe Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Glu Tyr Ile Pro Asn Asn Pro Ala Asn
        35                  40                  45

Pro Lys Phe Ile Tyr Thr Gln His Asp Gln Leu Tyr Met Ser Val Leu
    50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110

Gly His Asp Ala Glu Gly Leu Ser Tyr Ile Ser Gln Val Pro Phe Ala
        115                 120                 125

Ile Val Asp Leu Arg Asn Met His Thr Val Lys Val Asp Ile His Ser
    130                 135                 140

Gln Thr Ala Trp Val Glu Ala Gly Ala Thr Leu Gly Glu Val Tyr Tyr
145                 150                 155                 160

Trp Ile Asn Glu Met Asn Glu Asn Phe Ser Phe Pro Gly Gly Tyr Cys
                165                 170                 175

Pro Thr Val Gly Val Gly Gly His Phe Ser Gly Gly Gly Tyr Gly Ala
            180                 185                 190
```

```
Leu Met Arg Asn Tyr Gly Leu Ala Ala Asp Asn Ile Ile Asp Ala His
            195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Glu Asn Phe Val Ile
225                 230                 235                 240

Ile Ala Ala Trp Lys Ile Lys Leu Val Val Pro Ser Lys Ala Thr
                245                 250                 255

Ile Phe Ser Val Lys Lys Asn Met Glu Ile His Gly Leu Val Lys Leu
                260                 265                 270

Phe Asn Lys Trp Gln Asn Ile Ala Tyr Lys Tyr Asp Lys Asp Leu Met
            275                 280                 285

Leu Thr Thr His Phe Arg Thr Arg Asn Ile Thr Asp Asn His Gly Lys
    290                 295                 300

Asn Lys Thr Thr Val His Gly Tyr Phe Ser Ser Ile Phe Leu Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Leu Ser Trp Ile Asp Thr Thr Ile
                340                 345                 350

Phe Tyr Ser Gly Val Val Asn Tyr Asn Thr Ala Asn Phe Lys Lys Glu
            355                 360                 365

Ile Leu Leu Asp Arg Ser Ala Gly Lys Lys Thr Ala Phe Ser Ile Lys
    370                 375                 380

Leu Asp Tyr Val Lys Lys Leu Ile Pro Glu Thr Ala Met Val Lys Ile
385                 390                 395                 400

Leu Glu Lys Leu Tyr Glu Glu Val Gly Val Gly Met Tyr Val Leu
                405                 410                 415

Tyr Pro Tyr Gly Gly Ile Met Asp Glu Ile Ser Glu Ser Ala Ile Pro
            420                 425                 430

Phe Pro His Arg Ala Gly Ile Met Tyr Glu Leu Trp Tyr Thr Ala Thr
    435                 440                 445

Trp Glu Lys Gln Glu Asp Asn Glu Lys His Ile Asn Trp Val Arg Ser
450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn Pro Glu Ser
                485                 490                 495

Pro Asn Asn Tyr Thr Gln Ala Arg Ile Trp Gly Glu Lys Tyr Phe Gly
                500                 505                 510

Lys Asn Phe Asn Arg Leu Val Lys Val Lys Thr Lys Ala Asp Pro Asn
            515                 520                 525

Asn Phe Phe Arg Asn Glu Gln Ser Ile Pro Pro Leu Pro Pro Arg His
    530                 535                 540

His
545

<210> SEQ ID NO 5
<211> LENGTH: 1638
<212> TYPE: DNA
<213> ORGANISM: Cannabis sativa

<400> SEQUENCE: 5
atgaagtact caacattctg tttttggtat gtttgcaaga taatattttt ctttctctca      60
```

```
ttcaatatcc aaatttcaat agctaatcct caagaaaact tccttaaatg cttctcacaa    120
tatattccca ccaatgtaac aaatgcaaaa ctcgtataca ctcaacacga ccaatttat     180
atgtctatcc taaattcgac catacaaaat cttagattta cctctgacac aaccccaaaa    240
ccacttgtta tcatcactcc tttaaatgtc tcccatatcc aaggcactat tctatgctcc    300
aagaaagttg gcttgcagat tcgaactcga agcggtggtc atgatgctga gggcatgtcc    360
tacatatctc aagtcccatt tgttatagta gacttgagaa acatgcattc ggtcaaaata    420
gatgttcata gccaaactgc atgggttgaa gccggagcta cccttggaga gtttattat     480
tggatcaatg agaacaatga gaatcttagt tttcctgctg ggtactgccc tactgttggc    540
gcgggtggac actttagtgg aggaggctat ggagcattga tgcgaaatta tggcctcgcg    600
gctgataata tcattgatgc gcacttagtc aatgttgatg aaaagttttt agatcgaaaa    660
tccatggggg aagatttgtt tgggctata cgtggtggtg gaggagaaaa ctttggaatc     720
attgcagcgt ggaaaattag acttgttgct gtcccatcaa tgtctactat attcagtgtt    780
aaaaagaaca tggagataca tgagcttgtc aagttagtta caaatggca aaatattgct      840
tacatgtatg aaaagaatt attactcttt actcactta taaccaggaa tattacagat       900
aatcaaggga agaataagac aacaatacac agttacttct cctccatttt ccatggtgga    960
gtggatagtc tagtcgactt gatgaacaag agctttcctg aattgggtat taaaaaaaca   1020
gattgcaaac agttgagctg gattgatact atcatcttct acagtggtct tgtaaattac   1080
aacacaacta attttaaaaa agaaattttg cttgatagat caggtgggcg gaaggcggct   1140
ttctcgatta gttagacta tgttaagaaa ccgattccag aaaccgcaat ggtcacaatt    1200
ttggaaaaat tatatgaaga agatgtagga gttgggatgt tgtgttttta cccttatggt   1260
ggtataatgg atgagatttc agaatcagca attccattcc ctcatcgagc tggaatcatg   1320
tatgaaattt ggtacatagc ttcatgggag aagcaagaag ataatgaaaa gcatataaac   1380
tggattcgga atgtttataa tttcacgact ccttatgtgt cccaaaatcc aagaatggcg   1440
tatctcaatt atagggacct tgatttagga aaaactaatt tcgagagtcc taataattac   1500
acacaagcac gtatttgggg tgaaaagtat tttggtaaaa attttaatag gttagtaaaa   1560
gtaaaaacca aggttgatcc cgataatttc tttagaaacg aacaaagcat cccacctctt   1620
cccctacgtc atcattaa                                                 1638
```

<210> SEQ ID NO 6
<211> LENGTH: 545
<212> TYPE: PRT
<213> ORGANISM: Cannabis sativa

<400> SEQUENCE: 6

```
Met Lys Tyr Ser Thr Phe Cys Phe Trp Tyr Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Gln Tyr Ile Pro Thr Asn Val Thr Asn
        35                  40                  45

Ala Lys Leu Val Tyr Thr Gln His Asp Gln Phe Tyr Met Ser Ile Leu
    50                  55                  60

Asn Ser Thr Ile Gln Asn Leu Arg Phe Thr Ser Asp Thr Thr Pro Lys
65                  70                  75                  80

Pro Leu Val Ile Ile Thr Pro Leu Asn Val Ser His Ile Gln Gly Thr
                85                  90                  95
```

```
Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
            115                 120                 125

Ile Val Asp Leu Arg Asn Met His Ser Val Lys Ile Asp Val His Ser
130                 135                 140

Gln Thr Ala Trp Val Glu Ala Gly Ala Thr Leu Gly Glu Val Tyr Tyr
145                 150                 155                 160

Trp Ile Asn Glu Asn Asn Glu Asn Leu Ser Phe Pro Ala Gly Tyr Cys
                165                 170                 175

Pro Thr Val Gly Ala Gly Gly His Phe Ser Gly Gly Tyr Gly Ala
            180                 185                 190

Leu Met Arg Asn Tyr Gly Leu Ala Ala Asp Asn Ile Ile Asp Ala His
            195                 200                 205

Leu Val Asn Val Asp Gly Lys Val Leu Asp Arg Lys Ser Met Gly Glu
210                 215                 220

Asp Leu Phe Trp Ala Ile Arg Gly Gly Gly Gly Glu Asn Phe Gly Ile
225                 230                 235                 240

Ile Ala Ala Trp Lys Ile Arg Leu Val Ala Val Pro Ser Met Ser Thr
            245                 250                 255

Ile Phe Ser Val Lys Lys Asn Met Glu Ile His Glu Leu Val Lys Leu
            260                 265                 270

Val Asn Lys Trp Gln Asn Ile Ala Tyr Met Tyr Glu Lys Glu Leu Leu
            275                 280                 285

Leu Phe Thr His Phe Ile Thr Arg Asn Ile Thr Asp Asn Gln Gly Lys
            290                 295                 300

Asn Lys Thr Thr Ile His Ser Tyr Phe Ser Ser Ile Phe His Gly Gly
305                 310                 315                 320

Val Asp Ser Leu Val Asp Leu Met Asn Lys Ser Phe Pro Glu Leu Gly
            325                 330                 335

Ile Lys Lys Thr Asp Cys Lys Gln Leu Ser Trp Ile Asp Thr Ile Ile
            340                 345                 350

Phe Tyr Ser Gly Leu Val Asn Tyr Asn Thr Thr Asn Phe Lys Lys Glu
            355                 360                 365

Ile Leu Leu Asp Arg Ser Gly Gly Arg Lys Ala Ala Phe Ser Ile Lys
370                 375                 380

Leu Asp Tyr Val Lys Lys Pro Ile Pro Glu Thr Ala Met Val Thr Ile
385                 390                 395                 400

Leu Glu Lys Leu Tyr Glu Glu Asp Val Gly Val Gly Met Phe Val Phe
            405                 410                 415

Tyr Pro Tyr Gly Gly Ile Met Asp Glu Ile Ser Glu Ser Ala Ile Pro
            420                 425                 430

Phe Pro His Arg Ala Gly Ile Met Tyr Glu Ile Trp Tyr Ile Ala Ser
            435                 440                 445

Trp Glu Lys Gln Glu Asp Asn Glu Lys His Ile Asn Trp Ile Arg Asn
            450                 455                 460

Val Tyr Asn Phe Thr Thr Pro Tyr Val Ser Gln Asn Pro Arg Met Ala
465                 470                 475                 480

Tyr Leu Asn Tyr Arg Asp Leu Asp Leu Gly Lys Thr Asn Phe Glu Ser
            485                 490                 495

Pro Asn Asn Tyr Thr Gln Ala Arg Ile Trp Gly Glu Lys Tyr Phe Gly
            500                 505                 510
```

```
Lys Asn Phe Asn Arg Leu Val Lys Val Lys Thr Lys Val Asp Pro Asp
        515                 520                 525

Asn Phe Phe Arg Asn Glu Gln Ser Ile Pro Pro Leu Pro Leu Arg His
        530                 535                 540

His
545

<210> SEQ ID NO 7
<211> LENGTH: 1638
<212> TYPE: DNA
<213> ORGANISM: Cannabis sativa

<400> SEQUENCE: 7
atgaagtact caacattctg tttttggtat gtttgcaaga taatattttt ctttctctca      60
ttcaatatcc aaatttcaat agctaatcct caagaaaact tccttaaatg cttctcacaa    120
tatattccca ccaatgtaac aaatgcaaaa ctcgtataca gtcaacacga ccaattttat    180
atgtctatcc taaattcgac catacaaaat cttagattta cctctgaaac aaccccaaaa    240
ccacttgtta tcatcactcc tttaaatgtc tcccatatcc aaggcactat tctatgctcc    300
aagaaagttg gcttgcagat tcgaactcga agcggtggtc atgatgctga gggcatgtcc    360
tacatatctg aagtcccatt tgttatagta gacttgagaa acatgcattc ggtcaaaata    420
gatgttcata gccaaactgc atgggttgaa gccggagcta cccttggaga gtttattat    480 tggatcaatg agaacaatga gaatcttagt tttcctgctg gtactgccc tactgttggc    540 gcgggtggac actttagtgg aggaggctat ggagcattga tgcgaaatta tggcctcgcg    600
gctgataata tcattgatgc gcacttagtc aatgttgatg gaaaagtttt agatcgaaaa    660
tccatggggg aagatttgtt tgggctata cgtggtggtg gaggagaaaa ctttggaatc    720
attgcagcgt ggaaaattag acttgttgct gtcccatcaa tgtctactat attcagtgtt    780
aaaaagaaca tggagataca tgagcttgtc aagttagtta acaaatggca aaatattgct    840
tacatgtatg aaaagaatt attactcttt actcacttta taaccaggaa tattacagat    900
aatcaaggga gaataagac aacaatacac agttacttct cctccatttt ccatggtgga    960
gtggatagtc tagtcgactt gatgaacaag agctttcctg aattgggtat aaaaaaaaca   1020
gattgcaaac agttgagctg gattgatact atcatcttct acagtggtgt tgtaaattac   1080
aacacaacta attttaaaaa agaaattttg cttgatagat caggtgggcg gaaggcggct   1140
ttctcgatta gttagacta tgttaagaaa ccgattccag aaaccgcaat ggtcacaatt   1200
ttggaaaaat tatatgaaga agatgtagga gttgggatgt tgtgttttta cccttatggt   1260
ggtataatgg atgagatttc agaatcagca attccattcc ctcatcgagc tggaatcatg    1320 tatgaaatt ggtacatagc ttcatgggag aagcaagaag ataatgaaaa gcatataaac    1380
tggattcgga atgtttataa tttcacgact ccttatgtgt cccaaaatcc aagaatggcg    1440
tatctcaatt atagggacct tgatttagga aaaactaatt tcgagagtcc taataattac    1500
acacaagcac gtatttgggg tgaaaagtat tttggtaaaa atttaatag gttagtaaaa   1560 gtaaaaacca aggttgatcc cgataatttc tttagaaacg aacaaagcat cccacctctt    1620
cccctacgtc atcattaa                                                 1638

<210> SEQ ID NO 8
<211> LENGTH: 545
<212> TYPE: PRT
<213> ORGANISM: Cannabis sativa
```

<400> SEQUENCE: 8

```
Met Lys Tyr Ser Thr Phe Cys Phe Trp Tyr Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Gln Tyr Ile Pro Thr Asn Val Thr Asn
        35                  40                  45

Ala Lys Leu Val Tyr Ser Gln His Asp Gln Phe Tyr Met Ser Ile Leu
    50                  55                  60

Asn Ser Thr Ile Gln Asn Leu Arg Phe Thr Ser Glu Thr Thr Pro Lys
65                  70                  75                  80

Pro Leu Val Ile Ile Thr Pro Leu Asn Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Glu Val Pro Phe Val
        115                 120                 125

Ile Val Asp Leu Arg Asn Met His Ser Val Lys Ile Asp Val His Ser
130                 135                 140

Gln Thr Ala Trp Val Glu Ala Gly Ala Thr Leu Gly Glu Val Tyr Tyr
145                 150                 155                 160

Trp Ile Asn Glu Asn Asn Glu Asn Leu Ser Phe Pro Ala Gly Tyr Cys
                165                 170                 175

Pro Thr Val Gly Ala Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Arg Leu Val Ala Val Pro Ser Met Ser Thr
                245                 250                 255

Ile Phe Ser Val Lys Lys Asn Met Glu Ile His Glu Leu Val Lys Leu
            260                 265                 270

Val Asn Lys Trp Gln Asn Ile Ala Tyr Met Tyr Glu Lys Glu Leu Leu
        275                 280                 285

Leu Phe Thr His Phe Ile Thr Arg Asn Ile Thr Asp Asn Gln Gly Lys
    290                 295                 300

Asn Lys Thr Thr Ile His Ser Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Gln Leu Ser Trp Ile Asp Thr Ile Ile
            340                 345                 350

Phe Tyr Ser Gly Val Val Asn Tyr Asn Thr Thr Asn Phe Lys Lys Glu
        355                 360                 365

Ile Leu Leu Asp Arg Ser Gly Arg Lys Ala Phe Ser Ile Lys
    370                 375                 380

Leu Asp Tyr Val Lys Lys Pro Ile Pro Glu Thr Ala Met Val Thr Ile
385                 390                 395                 400

Leu Glu Lys Leu Tyr Glu Glu Asp Val Gly Val Gly Met Phe Val Phe
                405                 410                 415
```

```
Tyr Pro Tyr Gly Gly Ile Met Asp Glu Ile Ser Glu Ser Ala Ile Pro
                420                 425                 430

Phe Pro His Arg Ala Gly Ile Met Tyr Glu Ile Trp Tyr Ile Ala Ser
            435                 440                 445

Trp Glu Lys Gln Glu Asp Asn Glu Lys His Ile Asn Trp Ile Arg Asn
        450                 455                 460

Val Tyr Asn Phe Thr Thr Pro Tyr Val Ser Gln Asn Pro Arg Met Ala
465                 470                 475                 480

Tyr Leu Asn Tyr Arg Asp Leu Asp Leu Gly Lys Thr Asn Phe Glu Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Val Asp Pro Asp
        515                 520                 525

Asn Phe Phe Arg Asn Glu Gln Ser Ile Pro Pro Leu Pro Leu Arg His
530                 535                 540

His
545

<210> SEQ ID NO 9
<211> LENGTH: 1638
<212> TYPE: DNA
<213> ORGANISM: Cannabis sativa

<400> SEQUENCE: 9
atgaagtact caacattctg tttttggtat gtttgcaaga taatattttt ctttctctca      60
ttcaatatcc aaatttcaat agctaatcct caagaaaact tccttaaatg cttctcacaa     120
tatattccca ccaatgtaac aaatgcaaaa ctcgtataca ctcaacacga ccaattttat     180
atgtctatcc taaattcgac catacaaaat cttagattta cctctgacac aaccccaaaa     240
ccacttgtta tcatcactcc tttaaatgtc tcccatatcc aaggcactat tctatgctcc     300
aagaaagttg gcttgcagat tcgaactcga agcggtggtc atgatgctga gggcatgtcc     360
tacatatctc aagtcccatt tgttatagta gacttgagaa acatgcattc ggtcaaaata     420
gatgttcata gccaaactgc atgggttgaa gccggagcta cccttggaga agtttattat     480
tggatcaatg agaacaatga gaatcttagt tttcctgctg gtactgcccc tactgttggc     540
gcgggtggac actttagtgg aggaggctat ggagcattga tgcgaaatta tggcctcgcg     600
gctgataata tcattgatgc gcacttagtc aatgttgatg aaaagtttt agatcgaaaa     660 tccatggggg aagatttgtt tgggctata cgtggtggtg gaggagaaaa ctttggaatc     720
attgcagcgt ggaaaattag acttgttgct gtcccatcaa tgtctactat attcagtgtt     780
aaaaagaaca tggagataca tgagcttgtc aagttagtta caaatggca aaatattgct     840 tacatgtatg aaaagagaatt attactcttt actcacttta taaccaggaa tattacagat     900
aatcaaggga agaataagac aacaatacac agttacttct cctccatttt ccatggtgga     960
gtggatagtc tagtcgactt gatgaacaag agctttcctg aattgggtat taaaaaaaca    1020
gattgcaaac agttgagctg gattgatact atcatcttct acagtggtct tgtaaattac    1080
aacactacta atttaaaaaa agaaattttg cttgatagat caggtgggcg aaggcggct    1140 ttctcgatta agttagacta tgttaagaaa ccgattccag aaaccgcaat ggtcacaatt    1200 tggaaaaat tatatgaaga agatgtagga gttgggatgt tgtgttttta cccttatggt    1260
ggtataatgg atgagatttc agaatcagca attccattcc ctcatcgagc tggaatcatg    1320
```

```
tatgaaattt ggtacatagc ttcatgggag aagcaagaag ataatgaaaa gcatataaac    1380
tggattcgga atgtttataa tttcacgact ccttatgtgt cccaaaatcc aagaatggcg    1440
tatctcaatt ataggaacct tgatttagga aaaactaatt tcgagagtcc taataattac    1500
acacaagcac gtatttgggg tgaaaagtat tttggtaaaa attttaatag gttagtaaaa    1560
gtaaaaacca aggttgatcc cgataatttc tttagaaacg aacaaagcat cccacctctt    1620
cccctgcgtc atcattaa                                                  1638
```

<210> SEQ ID NO 10
<211> LENGTH: 545
<212> TYPE: PRT
<213> ORGANISM: Cannabis sativa

<400> SEQUENCE: 10

```
Met Lys Tyr Ser Thr Phe Cys Phe Trp Tyr Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Gln Tyr Ile Pro Thr Asn Val Thr Asn
        35                  40                  45

Ala Lys Leu Val Tyr Thr Gln His Asp Gln Phe Tyr Met Ser Ile Leu
    50                  55                  60

Asn Ser Thr Ile Gln Asn Leu Arg Phe Thr Ser Asp Thr Thr Pro Lys
65                  70                  75                  80

Pro Leu Val Ile Ile Thr Pro Leu Asn Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Ile Val Asp Leu Arg Asn Met His Ser Val Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Asn Asn Glu Asn Leu Ser Phe Pro Ala Gly Tyr Cys
                165                 170                 175

Pro Thr Val Gly Ala Gly Gly His Phe Ser Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Arg Leu Val Ala Val Pro Ser Met Ser Thr
                245                 250                 255

Ile Phe Ser Val Lys Lys Asn Met Glu Ile His Glu Leu Val Lys Leu
            260                 265                 270

Val Asn Lys Trp Gln Asn Ile Ala Tyr Met Tyr Glu Lys Glu Leu Leu
        275                 280                 285

Leu Phe Thr His Phe Ile Thr Arg Asn Ile Thr Asp Asn Gln Gly Lys
    290                 295                 300

Asn Lys Thr Thr Ile His Ser Tyr Phe Ser Ser Ile Phe His Gly Gly
```

```
                305                 310                 315                 320
Val Asp Ser Leu Val Asp Leu Met Asn Lys Ser Phe Pro Glu Leu Gly
                    325                 330                 335
Ile Lys Lys Thr Asp Cys Lys Gln Leu Ser Trp Ile Asp Thr Ile Ile
                    340                 345                 350
Phe Tyr Ser Gly Leu Val Asn Tyr Asn Thr Thr Asn Phe Lys Lys Glu
                    355                 360                 365
Ile Leu Leu Asp Arg Ser Gly Arg Lys Ala Ala Phe Ser Ile Lys
                370                 375                 380
Leu Asp Tyr Val Lys Lys Pro Ile Pro Glu Thr Ala Met Val Thr Ile
385                 390                 395                 400
Leu Glu Lys Leu Tyr Glu Asp Val Gly Val Gly Met Phe Val Phe
                    405                 410                 415
Tyr Pro Tyr Gly Gly Ile Met Asp Glu Ile Ser Glu Ser Ala Ile Pro
                    420                 425                 430
Phe Pro His Arg Ala Gly Ile Met Tyr Glu Ile Trp Tyr Ile Ala Ser
                    435                 440                 445
Trp Glu Lys Gln Glu Asp Asn Glu Lys His Ile Asn Trp Ile Arg Asn
                450                 455                 460
Val Tyr Asn Phe Thr Thr Pro Tyr Val Ser Gln Asn Pro Arg Met Ala
465                 470                 475                 480
Tyr Leu Asn Tyr Arg Asp Leu Asp Leu Gly Lys Thr Asn Phe Glu Ser
                    485                 490                 495
Pro Asn Asn Tyr Thr Gln Ala Arg Ile Trp Gly Glu Lys Tyr Phe Gly
                    500                 505                 510
Lys Asn Phe Asn Arg Leu Val Lys Val Lys Thr Lys Val Asp Pro Asp
                    515                 520                 525
Asn Phe Phe Arg Asn Glu Gln Ser Ile Pro Pro Leu Pro Leu Arg His
                530                 535                 540
His
545

<210> SEQ ID NO 11
<211> LENGTH: 1638
<212> TYPE: DNA
<213> ORGANISM: Cannabis sativa

<400> SEQUENCE: 11
atgaattgct caacattctc cttttggttt gtttgcaaaa taatattttt ctttctctca    60
ttcaatatcc aaatttcaat agctaatcct caagaaaact tccttaaatg cttctcggaa   120
tatattccta caatccagc aaatccaaaa ttcatataca ctcaacacga ccaattgtat   180
atgtctgtcc tgaattcgac aatacaaaat cttagattca cctctgatac aaccccaaaa   240
ccactcgtta ttgtcactcc ttcaaatgtc tcccatatcc aggccagtat tctctgctcc   300
aagaaagttg ttttgcagat tcgaactcga agcggtggcc atgatgctga gggtttgtcc   360
tacatatctc aagtcccatt tgctatagta gacttgagaa acatgcatac ggtcaaagta   420
gatattcata gccaaactgc gtgggttgaa gccggagcta cccttggaga agtttattat   480
tggatcaatg agatgaatga gaatttttagt tttcctggtg ggtattgccc tactgttggc   540
gtaggtggac actttagtgg aggaggctat ggagcattga tgcgaaatta tggccttgcg   600
gctgataata tcattgatgc acacttagtc aatgttgatg aaaagttct agatcgaaaa   660 tccatgggag aagatctatt tttgggctata cgtggtggag gaggagaaaa ctttggaatc   720
```

```
attgcagcat ggaaaatcaa acttgttgtt gtcccatcaa aggctactat attcagtgtt    780
aaaaagaaca tggagataca tgggcttgtc aagttattta acaaatggca aaatattgct    840
tacaagtatg acaaagattt aatgctcacg actcacttca gaactaggaa tattacagat    900
aatcatggga agaataagac tacagtacat ggttacttct cttccatttt tcttggtgga    960
gtggatagtc tagttgactt gatgaacaag agctttcctg agttgggtat taaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta agttagacta tgttaagaaa ctaatacctg aaactgcaat ggtcaaaatt   1200
ttggaaaaat tatatgaaga agaggtagga gttgggatgt atgtgttgta cccttacggt   1260
ggtataatgg atgagatttc agaatcagca attccattcc ctcatcgagc tggaataatg   1320
tatgaacttt ggtacactgc tacctgggag aagcaagaag ataacgaaaa gcatataaac   1380
tgggttcgaa gtgtttataa tttcacaact ccttatgtgt cccaaaatcc aagattggcg   1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca aagctgatcc caataatttt tttagaaacg aacaaagtat cccacctctt   1620
ccaccgcgtc atcattaa                                                  1638

<210> SEQ ID NO 12
<211> LENGTH: 545
<212> TYPE: PRT
<213> ORGANISM: Cannabis sativa

<400> SEQUENCE: 12

Met Asn Cys Ser Thr Phe Ser Phe Trp Phe Val Cys Lys Ile Ile Phe
  1               5                  10                  15

Phe Phe Leu Ser Phe Asn Ile Gln Ile Ser Ile Ala Asn Pro Gln Glu
                 20                  25                  30

Asn Phe Leu Lys Cys Phe Ser Glu Tyr Ile Pro Asn Asn Pro Ala Asn
             35                  40                  45

Pro Lys Phe Ile Tyr Thr Gln His Asp Gln Leu Tyr Met Ser Val Leu
         50                  55                  60

Asn Ser Thr Ile Gln Asn Leu Arg Phe Thr Ser Asp Thr Thr Pro Lys
 65                  70                  75                  80

Pro Leu Val Ile Val Thr Pro Ser Asn Val Ser His Ile Gln Ala Ser
                 85                  90                  95

Ile Leu Cys Ser Lys Lys Val Gly Leu Gln Ile Arg Thr Arg Ser Gly
            100                 105                 110

Gly His Asp Ala Glu Gly Leu Ser Tyr Ile Ser Gln Val Pro Phe Ala
        115                 120                 125

Ile Val Asp Leu Arg Asn Met His Thr Val Lys Val Asp Ile His Ser
    130                 135                 140

Gln Thr Ala Trp Val Glu Ala Gly Ala Thr Leu Gly Glu Val Tyr Tyr
145                 150                 155                 160

Trp Ile Asn Glu Met Asn Glu Asn Phe Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205
```

```
Leu Val Asn Val Asp Gly Lys Val Leu Asp Arg Lys Ser Met Gly Glu
210                 215                 220
Asp Leu Phe Trp Ala Ile Arg Gly Gly Gly Glu Asn Phe Gly Ile
225                 230                 235                 240
Ile Ala Ala Trp Lys Ile Lys Leu Val Val Pro Ser Lys Ala Thr
            245                 250                 255
Ile Phe Ser Val Lys Lys Asn Met Glu Ile His Gly Leu Val Lys Leu
            260                 265                 270
Phe Asn Lys Trp Gln Asn Ile Ala Tyr Lys Tyr Asp Lys Asp Leu Met
        275                 280                 285
Leu Thr Thr His Phe Arg Thr Arg Asn Ile Thr Asp Asn His Gly Lys
290                 295                 300
Asn Lys Thr Thr Val His Gly Tyr Phe Ser Ser Ile Phe Leu Gly Gly
305                 310                 315                 320
Val Asp Ser Leu Val Asp Leu Met Asn Lys Ser Phe Pro Glu Leu Gly
            325                 330                 335
Ile Lys Lys Thr Asp Cys Lys Glu Leu Ser Trp Ile Asp Thr Thr Ile
            340                 345                 350
Phe Tyr Ser Gly Val Val Asn Tyr Asn Thr Ala Asn Phe Lys Lys Glu
        355                 360                 365
Ile Leu Leu Asp Arg Ser Ala Gly Lys Lys Thr Ala Phe Ser Ile Lys
370                 375                 380
Leu Asp Tyr Val Lys Lys Leu Ile Pro Glu Thr Ala Met Val Lys Ile
385                 390                 395                 400
Leu Glu Lys Leu Tyr Glu Glu Val Gly Val Gly Met Tyr Val Leu
            405                 410                 415
Tyr Pro Tyr Gly Gly Ile Met Asp Glu Ile Ser Glu Ser Ala Ile Pro
            420                 425                 430
Phe Pro His Arg Ala Gly Ile Met Tyr Glu Leu Trp Tyr Thr Ala Thr
        435                 440                 445
Trp Glu Lys Gln Glu Asp Asn Glu Lys His Ile Asn Trp Val Arg Ser
450                 455                 460
Val Tyr Asn Phe Thr Thr Pro Tyr Val Ser Gln Asn Pro Arg Leu Ala
465                 470                 475                 480
Tyr Leu Asn Tyr Arg Asp Leu Asp Leu Gly Lys Thr Asn Pro Glu Ser
            485                 490                 495
Pro Asn Asn Tyr Thr Gln Ala Arg Ile Trp Gly Lys Tyr Phe Gly
            500                 505                 510
Lys Asn Phe Asn Arg Leu Val Lys Val Lys Thr Lys Ala Asp Pro Asn
        515                 520                 525
Asn Phe Phe Arg Asn Glu Gln Ser Ile Pro Pro Leu Pro Pro Arg His
530                 535                 540
His
545

<210> SEQ ID NO 13
<211> LENGTH: 23
<212> TYPE: DNA
<213> ORGANISM: Artificial Sequence
<220> FEATURE:
<223> OTHER INFORMATION: c395 Forward PCR Primer

<400> SEQUENCE: 13
tcacctctaa cacaacccca aaa                                          23
```

```
<210> SEQ ID NO 14
<211> LENGTH: 22
<212> TYPE: DNA
<213> ORGANISM: Artificial Sequence
<220> FEATURE:
<223> OTHER INFORMATION: c395 Reverse PCR Primer

<400> SEQUENCE: 14
ccaaaagaga tcttccccca ta                                                  22

<210> SEQ ID NO 15
<211> LENGTH: 20
<212> TYPE: DNA
<213> ORGANISM: Artificial Sequence
<220> FEATURE:
<223> OTHER INFORMATION: c8242 Forward PCR Primer

<400> SEQUENCE: 15
gcgttgtacc cttacggttg                                                     20

<210> SEQ ID NO 16
<211> LENGTH: 25
<212> TYPE: DNA
<213> ORGANISM: Artificial Sequence
<220> FEATURE:
<223> OTHER INFORMATION: c8242 Reverse PCR Primer

<400> SEQUENCE: 16
ttttgactct tgggatcatt tattc                                               25
```